US012788779B2

(12) United States Patent
Lebovits et al.

(10) Patent No.: US 12,788,779 B2
(45) Date of Patent: Nov. 10, 2026

(54) METHODS AND COMPOSITIONS FOR TREATING LUNG CONDITIONS

(71) Applicant: BRAINSTORM CELL THERAPEUTICS LTD., Petach Tikva (IL)

(72) Inventors: Chaim Lebovits, Jerusalem (IL); Revital Aricha, Giv'at Shmuel (IL); Yossef Levy, Modi'in (IL); Ralph Kern, New York, NY (US); Haggai Kaspi, Ganei Tikva (IL); Jonathan Semo, Giv'atayim (IL)

(73) Assignee: BRAINSTORM CELL THERAPEUTICS LTD., Petach Tikva (IL)

( * ) Notice: Subject to any disclaimer, the term of this patent is extended or adjusted under 35 U.S.C. 154(b) by 779 days.

(21) Appl. No.: 18/016,460

(22) PCT Filed: Jul. 20, 2021

(86) PCT No.: PCT/IL2021/050885

§ 371 (c)(1),
(2) Date: Jan. 17, 2023

(87) PCT Pub. No.: WO2022/018729

PCT Pub. Date: Jan. 27, 2022

(65) Prior Publication Data

US 2023/0310507 A1 Oct. 5, 2023

Related U.S. Application Data

(60) Provisional application No. 63/133,350, filed on Jan. 3, 2021, provisional application No. 63/053,780, filed on Jul. 20, 2020.

(51) Int. Cl.
*A61K 35/28* (2015.01)
*A61P 11/00* (2006.01)

(52) U.S. Cl.
CPC .............. *A61K 35/28* (2013.01); *A61P 11/00* (2018.01)

(58) Field of Classification Search
CPC .......... A61K 35/28; A61P 11/00; A61P 31/12; A61P 31/14; Y02A 50/30
See application file for complete search history.

(56) References Cited

U.S. PATENT DOCUMENTS

| | | | | |
|---|---|---|---|---|
| 2014/0065240 | A1* | 3/2014 | Mitsialis ................. | A61P 29/00 424/577 |
| 2015/0209389 | A1 | 7/2015 | Gothelf et al. | |
| 2016/0199413 | A1* | 7/2016 | Simonson .............. | A61K 35/28 435/325 |
| 2019/0153383 | A1 | 5/2019 | Chang et al. | |

FOREIGN PATENT DOCUMENTS

| | | | | |
|---|---|---|---|---|
| EP | 3 443 966 A1 | | 2/2019 | |
| WO | WO 2008/116157 A2 | | 9/2008 | |
| WO | WO 2012/125471 A1 | | 9/2012 | |
| WO | WO 2014/024183 A1 | | 2/2014 | |
| WO | WO 2015/016761 A2 | | 2/2015 | |
| WO | WO 2019/035880 | | 2/2019 | |
| WO | WO-2019092145 A1 | * | 5/2019 | ........... C12N 15/111 |
| WO | WO 2019/198077 A1 | | 10/2019 | |
| WO | WO 2020/006349 | | 1/2020 | |
| WO | WO 2021/176001 A1 | | 9/2021 | |
| WO | WO 2021/181399 A1 | | 9/2021 | |
| WO | WO 2021/198454 A1 | | 10/2021 | |
| WO | WO 2021/205459 A1 | | 10/2021 | |

OTHER PUBLICATIONS

Ra, J.C., Shin, I.S., Kim, S.H., Kang, S.K., Kang, B.C., Lee, H.Y., Kim, Y.J., Jo, J.Y., Yoon, E.J., Choi, H.J. and Kwon, E., 2011. Safety of intravenous infusion of human adipose tissue-derived mesenchymal stem cells in animals and humans. Stem cells and development, 20(8), pp. 1297-1308. (Year: 2011).*

Witwer, K.W., et al. 2019. Defining mesenchymal stromal cell (MSC)-derived small extracellular vesicles for therapeutic applications. Journal of extracellular vesicles, 8(1), p. 1609206 (Year: 2019).*

Gothelf, Y., Kaspi, H., Abramov, N. and Aricha, R., 2017. miRNA profiling of NurOwn®: mesenchymal stem cells secreting neurotrophic factors. Stem cell research & therapy, 8(1), p. 249. (Year: 2017).*

Abreu et al. "Extracellular vesicles derived from mesenchymal stromal cells: a therapeutic option in respiratory diseases?" Stem Cell Research & Therapy. 2016;7.

An et al. "miR-146a Attenuates Sepsis-Induced Myocardial Dysfunction by Suppressing IRAK1 and TRAF6 via Targeting ErbB4 Expression" Oxidative medicine and cellular longevity. Aug. 27, 2018;2018:7163057.

Ashcroft et al. "Simple method of estimating severity of pulmonary fibrosis on a numerical scale" Journal of clinical pathology. Apr. 1988;41(4):467-70.

Barnes et al. "Targeting potential drivers of COVID-19: Neutrophil extracellular traps" The Journal of experimental medicine. Jun. 1, 2020;217(6):e20200652.

(Continued)

*Primary Examiner* — Jeremy C Flinders
*Assistant Examiner* — Masudur Rahman
(74) *Attorney, Agent, or Firm* — PEARL COHEN LLP; Mark S Cohen

(57) ABSTRACT

The present invention provides compositions comprising mesenchymal stem cells (MSCs) and/or exosomes derived therefrom, mesenchymal stem cells secreting neurotrophic factors (MSC-NTFs) and/or exosomes derived therefrom, and methods for their use in treating adverse lung conditions, such as Coronavirus-related acute respiratory distress syndrome (ARDS). The disclosed methods are useful for treating coronavirus infection and associated conditions including pneumonia, acute respiratory distress syndrome, and related respiratory symptoms.

19 Claims, 20 Drawing Sheets

(56) References Cited

OTHER PUBLICATIONS

Bulut et al. "Mesenchymal stem cell derived extracellular vesicles: promising immunomodulators against autoimmune, autoinflammatory disorders and SARS-CoV-2 infection" Turkish journal of biology= Turk biyoloji dergisi. Jun. 21, 2020;44(3):273-82.
Carsana et al. "Pulmonary post-mortem findings in a series of COVID-19 cases from northern Italy: a two-centre descriptive study" The Lancet. Infectious diseases. Oct. 2020;20(10):1135-40.
Cascella et al. "Features, Evaluation, and Treatment of Coronavirus (COVID-19)" In StatPearls [Internet] Oct. 13, 2022. StatPearls Publishing.
Chambers et al. "Mesenchymal Stromal Cell Therapy for Chronic Lung Allograft Dysfunction: Results of a First-in-Man Study" Stem cells translational medicine. Apr. 2017;6(4):1152-7.
Chen et al. "Clinical and immunological features of severe and moderate coronavirus disease 2019" The Journal of clinical investigation. May 1, 2020;130(5):2620-9.
Cruz et al. "Stem-cell extracellular vesicles and lung repair" Stem cell investigation. Sep. 21, 2017;4:78.
Curley et al. "Mesenchymal stem cells enhance recovery and repair following ventilator-induced lung injury in the rat" Thorax. Jun. 2012;67(6):496-501.
Dominici et al. "Minimal criteria for defining multipotent mesenchymal stromal cells" The International Society for Cellular Therapy position statement. Cytotherapy. 2006;8(4):315-7.
Eggenhofer et al. "Mesenchymal stem cells are short-lived and do not migrate beyond the lungs after intravenous infusion" Frontiers in immunology. Sep. 26, 2012;3:297.
Fan et al. "Acute Respiratory Distress Syndrome: Advances in Diagnosis and Treatment" JAMA. Feb. 20, 2018;319(7):698-710.
Fischer et al. "Pulmonary passage is a major obstacle for intravenous stem cell delivery: the pulmonary first-pass effect" Stem cells and development. Jun. 2009;18(5):683-92.
Foronjy et al. "Leukemia inhibitory factor protects the lung during respiratory syncytial viral infection" BMC immunology. Oct. 3, 2014;15:41.
Gholamrezanezhad et al. "In vivo tracking of 111In-oxine labeled mesenchymal stem cells following infusion in patients with advanced cirrhosis" Nuclear medicine and biology. Oct. 2011;38(7):961-7.
Ghorani et al. "Experimental animal models for COPD: a methodological review" Tobacco Induced Diseases. 2017;15.
Gothelf et al. "miRNA profiling of NurOwn®: mesenchymal stem cells secreting neurotrophic factors" Stem Cell Research & Therapy. 2017;8.
Hassanpour et al. "The role of extracellular vesicles in COVID-19 virus infection" Infection, Genetics and Evolution. Nov. 2020;85:104422.
Herold et al. "Level of IL-6 predicts respiratory failure in hospitalized symptomatic COVID-19 patients" MedRxiv. Apr. 4, 2020:Apr. 2020.
Hu et al. "The hepatocyte growth factor-expressing character is required for mesenchymal stem cells to protect the lung injured by lipopolysaccharide in vivo" Stem cell research & therapy. Apr. 29, 2016;7(1):66.
Idell S. "Coagulation, fibrinolysis, and fibrin deposition in acute lung injury" Critical care medicine. Apr. 2003;31(4 Suppl):S213-20.
International Search Report for PCT Application No. PCT/IL2021/050885 dated Nov. 5, 2021.
Jiang et al. "Review of the Clinical Characteristics of Coronavirus Disease 2019 (COVID-19)" Journal of General Internal Medicine. May 2020;35(5):1545.
Keerthikumar et al. "ExoCarta: A web-based compendium of exosomal cargo" Journal of molecular biology. Feb. 2, 2016;428(4):688.
Keller et al. "Feasibility, Safety, and Tolerance of Mesenchymal Stem Cell Therapy for Obstructive Chronic Lung Allograft Dysfunction" Stem Cells Translational Medicine. Feb. 2018;7(2):161.
Khatri et al. "Mesenchymal stem cell-derived extracellular vesicles attenuate influenza virus-induced acute lung injury in a pig model" Stem Cell Research & Therapy. 2018;9.
Lalu et al. "Canadian Critical Care Trials Group. Safety of Cell Therapy with Mesenchymal Stromal Cells (SafeCell): A Systematic Review and Meta-Analysis of Clinical Trials" PLoS ONE. 2012;7(10).
Lee et al. "Therapeutic Use of Mesenchymal Stem Cell-Derived Extracellular Vesicles in Acute Lung Injury" Transfusion. Feb. 2019;59(Suppl 1):876.
Leibacher et al. "Biodistribution, migration and homing of systemically applied mesenchymal stem/stromal cells" Stem Cell Research & Therapy. 2016;7.
Leng et al. "Transplantation of ACE2-mesenchymal stem cells improves the outcome of patients with COVID-19 pneumonia" Aging and disease. Apr. 2020;11(2):216.
Li et al. "Mesenchymal stromal cell treatment prevents H9N2 avian influenza virus-induced acute lung injury in mice" Stem cell research & therapy. Oct. 28, 2016;7(1):159.
Li et al. "Longitudinal correlation of biomarkers of cardiac injury, inflammation, and coagulation to outcome in hospitalized COVID-19 patients" Journal of Molecular and Cellular Cardiology. Oct. 2020;147:74.
Liang et al. "Clinical remission of a critically ill COVID-19 patient treated by human umbilical cord mesenchymal stem cells: A case report" Medicine. Jul. 7, 2020;99(31).
Liao et al. "The landscape of lung bronchoalveolar immune cells in COVID-19 revealed by single-cell RNA sequencing" MedRxiv. Feb. 26, 2020:Feb. 2020.
Lin et al. "Coronavirus disease 2019 (COVID-19): cytokine storms, hyper-inflammatory phenotypes, and acute respiratory distress syndrome" Genes & diseases. Dec. 2020;7(4):520-7.
Liu et al. "Mesenchymal stem cells as a potential therapy for COVID-19" Stem cell research & therapy. May 4, 2020;11(1):169.
Liu et al. "Clinical and biochemical indexes from 2019-nCoV infected patients linked to viral loads and lung injury" Science China. Life Sciences. 2020;63(3):364.
Loy et al. "Therapeutic Implications of Human Umbilical Cord Mesenchymal Stromal Cells in Attenuating Influenza A (H5N1) Virus-Associated Acute Lung Injury" The Journal of infectious diseases. Jan. 7, 2019;219(2):186-96.
Mahida et al. "Extracellular Vesicles: A New Frontier for Research in Acute Respiratory Distress Syndrome" American journal of respiratory cell and molecular biology. Jul. 2020;63(1):15-24.
Masterson et al. "Modulating the distribution and fate of exogenously delivered MSCs to enhance therapeutic potential: knowns and unknowns" Intensive Care Medicine Experimental. Jul. 2019;7(Suppl 1).
Matthay et al. "Treatment with allogeneic mesenchymal stromal cells for moderate to severe acute respiratory distress syndrome (START study): a randomised phase 2a safety trial" The Lancet. Respiratory medicine. Feb. 2019;7(2):154.
Matute-Bello et al. "Acute Lung Injury in Animals Study Group. An official American Thoracic Society workshop report: features and measurements of experimental acute lung injury in animals" American journal of respiratory cell and molecular biology. May 2011;44(5):725-38.
Matute-Bello et al. "Animal models of acute lung injury" American Journal of Physiology-Lung Cellular and Molecular Physiology. Sep. 2008;295(3):L379.
Meng et al. "Amphiregulin inhibits TNF-α-induced alveolar epithelial cell death through EGFR signaling pathway" Biomedicine & pharmacotherapy= Biomedecine & pharmacotherapie. May 2020;125:109995.
Metcalfe SM. "COVID-19 lockdown: de-risking exit by protecting the lung with leukaemia inhibitory factor (LIF)" Medicine in Drug Discovery. Jun. 2020;6:100043.
Monsel et al. "Therapeutic Effects of Human Mesenchymal Stem Cell-derived Microvesicles in Severe Pneumonia in Mice" American journal of respiratory and critical care medicine. Aug. 1, 2015;192(3):324-36.
Murthy et al. Care for Critically Ill Patients With COVID-19. Jama. Apr. 21, 2020;323(15):1499-500.
Nie et al. "Growth Factor Gene-Modified Mesenchymal Stem Cells in Tissue Regeneration" Drug Design, Development and Therapy. 2020;14:1241.

(56) References Cited

OTHER PUBLICATIONS

Ogata-Suetsugu et al. "Amphiregulin suppresses epithelial cell apoptosis in lipopolysaccharide-induced lung injury in mice" Biochemical and biophysical research communications. Mar. 4, 2017;484(2):422-8.
Pedrazza et al. "Mesenchymal stem cells improves survival in LPS-induced acute lung injury acting through inhibition of NETs formation" Journal of cellular physiology. Dec. 2017;232(12):3552-64.
Petrou et al. "Safety and Clinical Effects of Mesenchymal Stem Cells Secreting Neurotrophic Factor Transplantation in Patients With Amyotrophic Lateral Sclerosis: Results of Phase 1/2 and 2a Clinical Trials" JAMA neurology. Mar. 2016;73(3):337-44.
Pfeiffer et al. "miR-146a, miR-146b, and miR-155 increase expression of IL-6 and IL-8 and support HSP10 in an in vitro sepsis model" PLoS ONE. 2017;12(6).
Potter et al. "Mesenchymal stem cell-derived extracellular vesicles attenuate pulmonary vascular permeability and lung injury induced by hemorrhagic shock and trauma" The journal of trauma and acute care surgery. Feb. 2018;84(2):245.
Quinton et al. "Leukemia inhibitory factor signaling is required for lung protection during pneumonia" Journal of immunology (Baltimore, Md.: 1950). Jun. 15, 2012;188(12):6300-8.
Ranieri et al. "Acute respiratory distress syndrome: the Berlin Definition" Jama. 2012;307(23):2526-33.
Remuzzi et al. "COVID-19 and Italy: what next?" Lancet (London, England). Apr. 11, 2020;395(10231):1225-8.
Ringdén et al. "Mesenchymal stem cells for treatment of therapy-resistant graft-versus-host disease" Transplantation. May 27, 2006;81(10):1390-7.
Roudsari et al. "Auxiliary role of mesenchymal stem cells as regenerative medicine soldiers to attenuate inflammatory processes of severe acute respiratory infections caused by COVID-19" Cell and Tissue Banking. 2020;21(3):405.
Sengupta et al. "Exosomes Derived from Bone Marrow Mesenchymal Stem Cells as Treatment for Severe COVID-19" Stem Cells and Development. Jun. 15, 2020;29(12):747.
Shah et al. "Mesenchymal stem cells-derived extracellular vesicles in acute respiratory distress syndrome: a review of current literature and potential future treatment options" Clinical and Translational Medicine. 2019;8.
Skendros et al. "Complement and tissue factor-enriched neutrophil extracellular traps are key drivers in COVID-19 immunothrombosis" The Journal of Clinical Investigation. Oct. 10, 2020;130(11):6151.
Song et al. "Exosomal miR-146a Contributes to the Enhanced Therapeutic Efficacy of Interleukin-1β-Primed Mesenchymal Stem Cells Against Sepsis" Stem cells (Dayton, Ohio). May 2017;35(5):1208-21.
Stakos et al. "Traps N'Clots: NET-Mediated Thrombosis and Related Diseases" Thrombosis and haemostasis. Mar. 2020;120(3):373-83.
Tsuchiya et al. "Therapeutic potential of mesenchymal stem cells and their exosomes in severe novel coronavirus disease 2019 (COVID-19) cases" Inflammation and regeneration. Jun. 22, 2020:40:14.
Ulich et al. "Intratracheal injection of LPS and cytokines. V. LPS induces expression of LIF and LIF inhibits acute inflammation" The American journal of physiology. Oct. 1994;267(4 Pt 1):L442-6.
Walter et al. "Mesenchymal stem cells: mechanisms of potential therapeutic benefit in ARDS and sepsis" The Lancet. Respiratory medicine. Dec. 2014;2(12):1016-26.
Wang et al. "Detection of SARS-CoV-2 in Different Types of Clinical Specimens" JAMA. May 5, 2020;323(18):1843.
Wang et al. "Clinical Characteristics of 138 Hospitalized Patients With 2019 Novel Coronavirus-Infected Pneumonia in Wuhan, China" JAMA. Mar. 17, 2020;323(11):1061-9.
Wang et al. "Mesenchymal stem cells microvesicles stabilize endothelial barrier function partly mediated by hepatocyte growth factor (HGF)" Stem cell research & therapy. Sep. 29, 2017;8(1):211.
Whyte et al. "Fibrinolytic abnormalities in acute respiratory distress syndrome (ARDS) and versatility of thrombolytic drugs to treat COVID-19" Journal of thrombosis and haemostasis: JTH. Jul. 2020;18(7):1548-55.
World Health Organization "Clinical management of severe acute respiratory infection (SARI) when COVID-19 disease is suspected: interim guidance, Mar. 13, 2020" World Health Organization; 2020.
Xiao et al. "Mesenchymal stern cells: current clinical progress in ARDS and COVID-19" Stem Cell Research & Therapy. 2020;11.
Xu et al. "Classically Activated Macrophages Protect against Lipopolysaccharide-induced Acute Lung Injury by Expressing Amphiregulin in Mice" Anesthesiology. May 2016;124(5):1086-99.
Yáñez-Mó et al. "Biological properties of extracellular vesicles and their physiological functions" Journal of Extracellular Vesicles. 2015;4.
Ye et al. "The pathogenesis and treatment of theCytokine Storm'in COVID-19" The Journal of Infection. Jun. 2020;80(6):607.
Yu et al. "Exosomes Derived from Mesenchymal Stem Cells" International Journal of Molecular Sciences. Mar. 2014;15(3):4142.
Zheng et al. "Mesenchymal stromal cell-derived extracellular vesicles: regenerative and immunomodulatory effects and potential applications in sepsis" Cell and tissue research. Oct. 2018;374(1):1-5.
Zheng et al. "Treatment of acute respiratory distress syndrome with allogeneic adipose-derived mesenchymal stem cells: a randomized, placebo-controlled pilot study" Respiratory Research. 2014;15(1):39.
Zhu et al. "Brief Report: A Novel Coronavirus from Patients with Pneumonia in China, 2019" The New England Journal of Medicine. Feb. 2, 2020;382(8):727.
Zhu et al. "Human mesenchymal stem cell microvesicles for treatment of *Escherichia coli* endotoxin-induced acute lung injury in mice" Stem cells (Dayton, Ohio). Jan. 2014;32(1):116-25.

* cited by examiner

METHODS AND COMPOSITIONS FOR TREATING LUNG CONDITIONS

BACKGROUND OF THE INVENTION

The body's respiratory system includes the nose, sinuses, mouth, throat (pharynx), voice box (larynx), windpipe (trachea), and lungs. Upper respiratory infections affect the parts of the respiratory tract that are higher in the body, including the nose, sinuses, and throat, while lower respiratory infections affect the airways and lungs.

Types of upper respiratory infections include the common cold (head cold), the mild flu, tonsillitis, laryngitis, and sinus infection. Of the upper respiratory infection symptoms, the most common is a cough. Lung infections may also lead to a stuffy or runny nose, sore throat, sneezing, achy muscles, and headache.

Lower respiratory infections may be found in lungs or breathing airways. They can be caused by viral infections like the severe flu or bacterial infections like tuberculosis. Lower respiratory infection symptoms include a severe cough that may produce mucus (phlegm), cause shortness of breath, chest tightness, and wheezing when exhaling.

The COVID-19 pandemic due to SARS-CoV-2 may present with mild, moderate, or severe illness. The severe clinical manifestations include pneumonia, acute respiratory distress syndrome (ARDS), sepsis, and septic shock.

In a still undetermined percentage of affected individuals, after about a week of illness, there is a sudden clinical worsening with rapidly evolving respiratory failure and multiple organ dysfunction (MOD) or failure (MOF).

The concern that COVID-19 may cause critical illness, respiratory failure and death is at the core of public anxiety. ARDS due to COVID-19 may be associated with a mortality rate of more than 50% and currently there is no effective curative treatment strategy to reverse ARDS, a type of respiratory failure associated with widespread inflammation and dysregulated cytokine production that can be demonstrated in bronchoalveolar lavage (BAL). In addition, despite recent advances and intensive care, ARDS may be accompanied by overwhelming systemic inflammation and multiorgan failure, and the combined impact on existing health care resources is unacceptably high. It has been demonstrated that COVID-19 viral load correlates with pulmonary function and outcomes and inflammatory biomarkers, suggesting that therapies that disrupt viral propagation and lung inflammatory disease may be synergistic. Clearly any therapy that can minimize the impact of COVID-19 on ARDS, sepsis and multiorgan failure is much needed.

Further, improved therapies and strategies are needed to tackle ongoing and future COVID-19 pandemics.

SUMMARY OF THE INVENTION

The present invention provides, in one aspect, a method for treating a viral lung infection or a symptom thereof in a patient in need, comprising administering to the patient a therapeutically-effective regime of a pharmaceutical composition comprising an active agent selected from the group consisting of (a) a plurality of multipotent mesenchymal stem cells (MSCs) or mesenchymal stem cells secreting neurotrophic factors (MSC-NTFs), (b) a plurality of small EVs (sEVs) derived from multipotent mesenchymal stem cells defined EXO-MSC or small EVs (sEVs) derived from MSC-NTFs (NurOwn) defined EXO-MSC-NTFs, and (c) a combination of MSCs or MSC-NTFs and EXO-MSCs or EXO-MSC-NTFs.

In certain embodiments, the therapeutically effective regime comprises a single administration of the active agent. In certain embodiments, the therapeutically effective regime comprises repeated administration of the active agent.

In certain embodiments, the active agent is MSCs. In certain embodiments, the active agent is a combination of MSCs and EXO-MSCs.

In certain embodiments, the active agent is MSC-NTFs.

In certain embodiments, the pharmaceutical composition comprises about $5\times10^6$ to about $300\times10^6$ MSCs.

In certain embodiments, the pharmaceutical composition comprises about $15\times10^6$ to about $100\times10^6$ MSCs.

In certain embodiments, the pharmaceutical composition comprises about $15\times10^6$ to about $20\times10^6$ MSCs.

In certain embodiments, the pharmaceutical composition comprises about $80\times10^6$ to about $100\times10^6$ MSCs.

In certain embodiments, the active agent is EXO-MSCs.

In certain embodiments, the active agent is EXO-MSC-NTFs.

In certain embodiments, the pharmaceutical composition comprises about $10^9$ to about $10^{12}$ EXO-MSCs or EXO-MSC-NTFs. In certain embodiments, the pharmaceutical composition comprises about $10^{10}$ to about $10^{12}$ EXO-MSCs or EXO-MSC-NTFs.

In certain embodiments, the pharmaceutical composition comprises about $3*10^{10}$ to about $3*10^{11}$ EXO-MSCs or EXO-MSC-NTFs.

In certain embodiments, the pharmaceutical composition comprises about $10^{11}$ EXO-MSCs or EXO-MSC-NTFs.

In certain embodiments, the total dose of the active agent administered to the patient is selected from the group consisting of (a) about $75\times10^6$ to about $500\times10^6$ MSCs, (b) about $5\times10^{11}$ EXO-MSCs or EXO-MSC-NTFs, and (c) a combination of about $75\times10^6$ to about $500\times10^6$ MSCs and about $5\times10^{11}$ EXO-MSCs or EXO-MSC-NTFs.

In certain embodiments, the MSCs comprise bone-marrow-derived MSCs (BM-MSCs).

In certain embodiments, the therapeutically effective regime comprises a single administration of the active agent. In certain embodiments, the therapeutically effective regime comprises repeated administration of the active agent.

In certain embodiments, the therapeutically effective regime comprises repeated administration of the active agent in different days.

In certain embodiments, the repeated administration comprises administration on at least five different days.

In certain embodiments, the repeated administration comprises administration on consecutive days.

In certain embodiments, the repeated administration comprises administration on alternate days.

In certain embodiments, the pharmaceutical composition further comprises an excipient.

In certain embodiments, the excipient is Plasma-Lyte A.

In certain embodiments, the excipient is DMEM.

In certain embodiments, the excipient is CryoStor® CS10 Freeze Media.

In certain embodiments, the volume of the pharmaceutical composition is between about 100 mL to about 120 mL.

In certain embodiments, the method described above comprises systemic administration of the pharmaceutical composition.

In certain embodiments, the method described above comprises intravenous administration of the pharmaceutical composition.

In certain embodiments, the method described above comprises intranasal administration of the pharmaceutical composition.

In certain embodiments, the method described above comprises inhalation administration of the pharmaceutical composition.

In certain embodiments, the method described above comprises intratracheal administration of the pharmaceutical composition.

In certain embodiments, the method described above comprises direct injection of the pharmaceutical composition.

In certain embodiments, the method described above comprises administration of the pharmaceutical composition by inhalation.

In certain embodiments, the symptom is selected from the group consisting of pneumonia, acute respiratory distress syndrome (ARDS), multi-organ failure, fever, dry cough, fatigue, sputum production, loss of smell, shortness of breath, muscle pain, joint pain, sore throat, headache, chills, nausea, vomiting, nasal congestion, and diarrhea.

In certain embodiments, the symptom is pneumonia.

In certain embodiments, the symptom is ARDS.

In certain embodiments, the viral lung infection is selected from the group consisting of a Coronavirus infection, a Severe acute respiratory syndrome (SARS) infection, a Middle East respiratory syndrome (MERS) infection, an Influenza virus infection, an Ebola virus infection, a rabies infection, a West Nile virus infection, a dengue virus infection, a respiratory syncytial virus (RSV) infection, and a Zika virus infection.

In certain embodiments, the viral lung infection is Coronavirus infection.

In certain embodiments, the active agent is selected from the group consisting of (a) MSC-NTFs, (b) EXO-MSC-NTFs, and (c) a combination of MSC-NTFs and EXO-MSC-NTFs.

Other aspects and features of the present disclosure will become apparent to those ordinarily skilled in the art upon review of the following description of specific embodiments in conjunction with the accompanying Figures.

BRIEF DESCRIPTION OF THE DRAWINGS

FIG. 8. Representative histologic micrographs of lung lesions.

FIG. 10. Broncho Alveolar fluid cytokine levels.

FIG. 11. Broncho Alveolar fluid cytokine levels.

FIG. 16. A schematic illustration of EXO-MSC or EXO-MSC-NTF or PBS as control administration to bleomycin sulfate induced pulmonary injury in mice. Treatment was provided either at the inflammatory phase (on day 1 and day 5, FIG. 16A and FIG. 16D) or at the fibrotic phase (on day 7 and day 10, FIG. 16B and FIG. 16E) to separately evaluate the effect of the exosomes on inflammation and fibrosis. One study group received daily treatments (days 5-12) via inhalation (FIG. 16C and FIG. 16F) and was compared to the two PBS controls (days 1, 5 and days 7, 10). Results are presented as Mean±SEM.

DETAILED DISCLOSURE OF THE INVENTION

Figure 1:
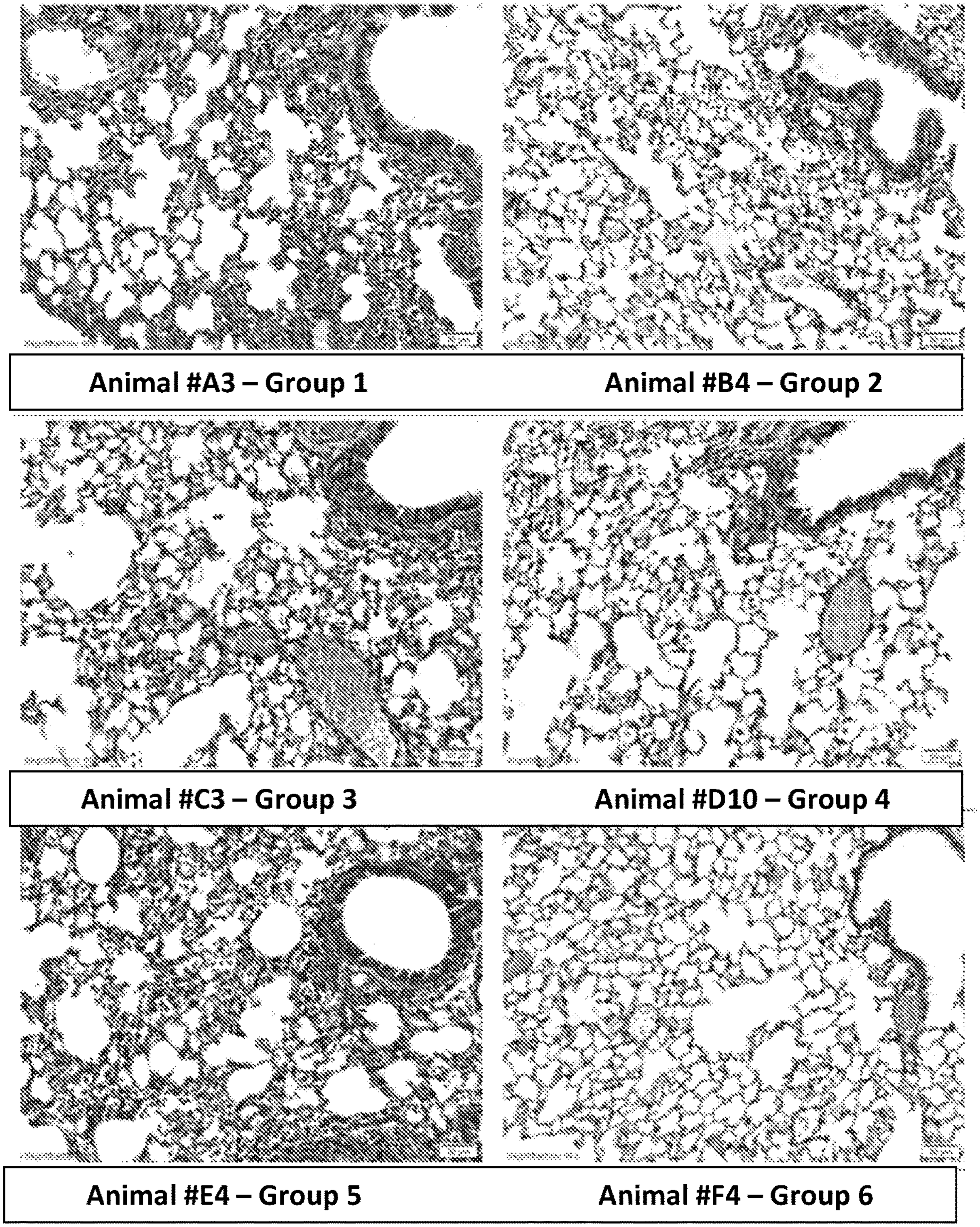
FIG. 1. Murine lung histopathological micrographs of lung lesions.

The present invention provides method, compositions, and therapeutic regimes for treating a variety of human conditions generally known as "viral lung infections" or "respiratory virus infections".

According to the principles of the present invention, a therapeutic drug, in a predetermined dose, is administered to patients according to a predetermined therapeutic regime, in order to both maximize the therapeutic effect of the therapeutic drug and minimize any inconvenience or risk to the treated patient.

As any person skilled in the art would appreciate, the use of different therapeutic drugs, of different doses, administered via different administration regimes, would likely result in different therapeutic outcomes.

The present invention provides, in one aspect, a method for treating a viral lung infection or a symptom thereof in a patient in need, comprising administering to the patient a therapeutically-effective regime of a pharmaceutical composition comprising an active agent selected from the group consisting of (a) a plurality of multipotent mesenchymal stem cells (MSCs) or MSC-NTFs, (b) a plurality of small EVs (sEVs) derived from multipotent mesenchymal stem cells defined EXO-MSCs or small EVs (sEVs) derived from MSC-NTFs (NurOwn) defined EXO-MSC-NTFs, and (c) a combination of MSCs or MSC-NTFs and EXO-MSCs or EXO-MSC-NTFs.

In certain embodiments, the therapeutically effective regime comprises a single administration of the active agent. In certain embodiments, the therapeutically effective regime comprises repeated administration of the active agent. In certain embodiments, the therapeutically effective regime comprises a plurality of administration events of the active agent. In certain embodiments, the therapeutically effective regime comprises a plurality of administration events of the same active agent. In certain embodiments, the therapeutically effective regime comprises a plurality of administration events of different active agents. In certain embodiments, the therapeutically effective regime comprises a single administration event of each different active agent. In certain embodiments, the therapeutically effective regime comprises administration of two different active agents. In certain embodiments, the therapeutically effective regime comprises administration of three different active agents.

In certain embodiments, the active agent is MSCs. In certain embodiments, the MSCs are administered at least 2 times to the patient. In certain embodiments, the MSCs are administered at least 3 times to the patient. In certain embodiments, the MSCs are administered at least 4 times to the patient. In certain embodiments, the MSCs are administered at least 5 times to the patient. In certain embodiments, the MSCs are administered 2 times to the patient. In certain embodiments, the MSCs are administered 3 times to the patient. In certain embodiments, the MSCs are administered 4 times to the patient. In certain embodiments, the MSCs are administered 5 times to the patient. In certain embodiments, the MSCs are administered no more than 2 times to the patient. In certain embodiments, the MSCs are administered no more than 3 times to the patient. In certain embodiments, the MSCs are administered no more than 4 times to the patient. In certain embodiments, the MSCs are administered no more than 5 times to the patient. In certain embodiments, the MSCs are administered 1 to 5 times to the patient. In certain embodiments, the MSCs are administered 2 to 5 times to the patient. In certain embodiments, the MSCs are administered 3 to 5 times to the patient. In certain embodiments, the MSCs are administered 4 to 5 times to the patient.

In certain embodiments, the MSCs are administered on day 1, day 3 and day 5. In certain embodiments, the MSCs are administered on day 1, day 3, day 5, day 7 and day 9.

In certain embodiments, the active agent is a combination of MSCs and EXO-MSCs. In certain embodiments, the combination of MSCs and EXO-MSCs is administered at least 2 times to the patient. In certain embodiments, the combination of MSCs and EXO-MSCs is administered at least 3 times to the patient. In certain embodiments, the combination of MSCs and EXO-MSCs is administered at least 4 times to the patient. In certain embodiments, the combination of MSCs and EXO-MSCs is administered at least 5 times to the patient. In certain embodiments, the combination of MSCs and EXO-MSCs is administered 2 times to the patient. In certain embodiments, the combination of MSCs and EXO-MSCs is administered 3 times to the patient. In certain embodiments, the combination of MSCs and EXO-MSCs is administered 4 times to the patient. In certain embodiments, the combination of MSCs and EXO-MSCs is administered 5 times to the patient. In certain embodiments, the combination of MSCs and EXO-MSCs is administered no more than 2 times to the patient. In certain embodiments, the combination of MSCs and EXO-MSCs is administered no more than 3 times to the patient. In certain embodiments, the combination of MSCs and EXO-MSCs is administered no more than 4 times to the patient. In certain embodiments, the combination of MSCs and EXO-MSCs is administered no more than 5 times to the patient. In certain embodiments, the combination of MSCs and EXO-MSCs is administered 1 to 5 times to the patient. In certain embodiments, the combination of MSCs and EXO-MSCs is administered 2 to 5 times to the patient. In certain embodiments, the combination of MSCs and EXO-MSCs is administered 3 to 5 times to the patient. In certain embodiments, the combination of MSCs and EXO-MSCs is administered 4 to 5 times to the patient.

In certain embodiments, the combination of MSCs and EXO-MSCs is administered on day 1, day 3 and day 5. In certain embodiments, the combination of MSCs and EXO-MSCs administered on day 1, day 3, day 5, day 7 and day 9.

In certain embodiments, the pharmaceutical composition comprises about $1\times10^5$ to about $1000\times10^7$ MSCs. In certain embodiments, the pharmaceutical composition comprises about $5\times10^5$ to about $300\times10^7$ MSCs. In certain embodiments, the pharmaceutical composition comprises about $1\times10^6$ to about $1000\times10^6$ MSCs. In certain embodiments, the pharmaceutical composition comprises about $5\times10^6$ to about $300\times10^6$ MSCs.

In certain embodiments, the pharmaceutical composition comprises about $5\times10^6$ to about $300\times10^6$ MSCs. In certain embodiments, the pharmaceutical composition comprises about $1\times10^6$ to about $200\times10^6$ MSCs. In certain embodiments, the pharmaceutical composition comprises about $15\times10^6$ to about $100\times10^6$ MSCs.

In certain embodiments, the pharmaceutical composition comprises about $5\times10^6$ to about $60\times10^6$ MSCs. In certain embodiments, the pharmaceutical composition comprises about $1\times10^6$ to about $40\times10^6$ MSCs. In certain embodiments, the pharmaceutical composition comprises about $15\times10^6$ to about $20\times10^6$ MSCs.

In certain embodiments, the pharmaceutical composition comprises about $20\times10^6$ to about $400\times10^6$ MSCs. In certain embodiments, the pharmaceutical composition comprises about $40\times10^6$ to about $200\times10^6$ MSCs. In certain embodiments, the pharmaceutical composition comprises about $80\times10^6$ to about $100\times10^6$ MSCs.

In certain embodiments, the active agent is EXO-MSCs. In certain embodiments, the EXO-MSCs are administered at least 2 times to the patient. In certain embodiments, the EXO-MSCs are administered at least 3 times to the patient. In certain embodiments, the EXO-MSCs are administered at least 4 times to the patient. In certain embodiments, the EXO-MSCs are administered at least 5 times to the patient. In certain embodiments, the EXO-MSCs are administered 2 times to the patient. In certain embodiments, the EXO-MSCs are administered 3 times to the patient. In certain embodiments, the EXO-MSCs are administered 4 times to the patient. In certain embodiments, the EXO-MSCs are administered 5 times to the patient. In certain embodiments, the EXO-MSCs are administered no more than 2 times to the patient. In certain embodiments, the EXO-MSCs are administered no more than 3 times to the patient. In certain embodiments, the EXO-MSCs are administered no more than 4 times to the patient. In certain embodiments, the EXO-MSCs are administered no more than 5 times to the patient. In certain embodiments, the EXO-MSCs are administered 1 to 5 times to the patient. In certain embodiments, the EXO-MSCs are administered 2 to 5 times to the patient. In certain embodiments, the EXO-MSCs are administered 3 to 5 times to the patient. In certain embodiments, the EXO-MSCs are administered 4 to 5 times to the patient.

In certain embodiments, the EXO-MSCs are administered on day 1, day 3 and day 5. In certain embodiments, the EXO-MSCs are administered on day 1, day 3, day 5, day 7 and day 9.

In certain embodiments, the active agent is EXO-MSC-NTFs. In certain embodiments, the EXO-MSC-NTFs are administered at least 2 times to the patient. In certain embodiments, the EXO-MSC-NTFs are administered at least 3 times to the patient. In certain embodiments, the EXO-MSC-NTFs are administered at least 4 times to the patient. In certain embodiments, the EXO-MSC-NTFs are administered at least 5 times to the patient. In certain embodiments, the EXO-MSC-NTFs are administered 2 times to the patient. In certain embodiments, the EXO-MSC-NTFs are administered 3 times to the patient. In certain embodiments, the EXO-MSC-NTFs are administered 4 times to the patient. In certain embodiments, the EXO-MSC-NTFs are administered 5 times to the patient. In certain embodiments, the EXO-MSC-NTFs are administered no more than 2 times to the patient. In certain embodiments, the EXO-MSC-NTFs are administered no more than 3 times to the patient. In certain embodiments, the EXO-MSC-NTFs are administered no more than 4 times to the patient. In certain embodiments, the EXO-MSC-NTFs are administered no more than 5 times to the patient. In certain embodiments, the EXO-MSC-NTFs are administered 1 to 5 times to the patient. In certain embodiments, the EXO-MSC-NTFs are administered 2 to 5 times to the patient. In certain embodiments, the EXO-MSC-NTFs are administered 3 to 5 times to the patient. In certain embodiments, the EXO-MSC-NTFs are administered 4 to 5 times to the patient.

In certain embodiments, the EXO-MSC-NTFs are administered on day 1, day 3 and day 5. In certain embodiments, the EXO-MSC-NTFs are administered on day 1, day 3, day 5, day 7 and day 9.

In certain embodiments, the pharmaceutical composition comprises about $10^9$ to about $10^{13}$ EXO-MSCs or EXO-MSC-NTFs. In certain embodiments, the pharmaceutical composition comprises about $3\times10^9$ to about $3\times10^{12}$ EXO-MSCs or EXO-MSC-NTFs. In certain embodiments, the pharmaceutical composition comprises about $10^9$ to about $10^{12}$ EXO-MSCs or EXO-MSC-NTFs. In certain embodiments, the pharmaceutical composition comprises about $10^{10}$ to about $10^{12}$ EXO-MSCs or EXO-MSC-NTFs.

In certain embodiments, the pharmaceutical composition comprises about $2*10^9$ to about $5*10^{11}$ EXO-MSCs or EXO-MSC-NTFs. In certain embodiments, the pharmaceutical composition comprises about $3*10^9$ to about $3*10^{11}$ EXO-MSCs or EXO-MSC-NTFs. In certain embodiments, the pharmaceutical composition comprises about $5*10^9$ to about $2*10^{11}$ EXO-MSCs or EXO-MSC-NTFs.

In certain embodiments, the pharmaceutical composition comprises about $2*10^{10}$ to about $5*10^{11}$ EXO-MSCs or EXO-MSC-NTFs. In certain embodiments, the pharmaceutical composition comprises about $3*10^{10}$ to about $3*10^{11}$ EXO-MSCs or EXO-MSC-NTFs. In certain embodiments, the pharmaceutical composition comprises about $5*10^{10}$ to about $2*10^{11}$ EXO-MSCs or EXO-MSC-NTFs.

In certain embodiments, the pharmaceutical composition comprises about $10^{11}$ EXO-MSCs or EXO-MSC-NTFs. In certain embodiments, the pharmaceutical composition comprises about $0.9\times10^{11}$ to about $1.1\times10^{11}$ EXO-MSCs or EXO-MSC-NTFs.

In certain embodiments, the total dose of the active agent administered to the patient is selected from the group consisting of (a) about $75\times10^5$ to about $500\times10^7$ MSCs, (b) about $5\times10^{10}$ to about $5\times10^{12}$ EXO-MSCs or EXO-MSC-NTFs, and (c) a combination of about $75\times10^5$ to about $500\times10^7$ MSCs and about $5\times10^9$ to about $5\times10^{12}$ EXO-MSCs or EXO-MSC-NTFs.

In certain embodiments, the total dose of the active agent administered to the patient is selected from the group consisting of (a) about $75\times10^5$ to about $500\times10^7$ MSCs, (b) about $5\times10^{10}$ to about $5\times10^{12}$ EXO-MSCs or EXO-MSC-NTFs, and (c) a combination of about $75\times10^5$ to about $500\times10^7$ MSCs and about $5\times10^{10}$ to about $5\times10^{12}$ EXO-MSCs or EXO-MSC-NTFs.

In certain embodiments, the total dose of the active agent administered to the patient is selected from the group consisting of (a) about $15\times10^6$ to about $250\times10^7$ MSCs, (b) about $1\times10^{11}$ to about $25\times10^{11}$ EXO-MSCs or EXO-MSC-NTFs, and (c) a combination of about $15\times10^6$ to about $250\times10^7$ MSCs and about $1\times10^{11}$ to about $25\times10^{11}$ EXO-MSCs or EXO-MSC-NTFs.

In certain embodiments, the total dose of the active agent administered to the patient is selected from the group consisting of (a) about $25\times10^6$ to about $150\times10^7$ MSCs, (b) about $1.5\times10^{11}$ to about $1.5\times10^{12}$ EXO-MSCs or EXO-MSC-NTFs, and (c) a combination of about $25\times10^6$ to about $150\times10^7$ MSCs and about $1.5\times10^{11}$ to about $1.5\times10^{12}$ EXO-MSCs or EXO-MSC-NTFs.

In certain embodiments, the total dose of the active agent administered to the patient is selected from the group consisting of (a) about $30\times10^6$ to about $100\times10^7$ MSCs, (b) about $2.5\times10^{11}$ to about $1\times10^{12}$ EXO-MSCs or EXO-MSC-NTFs, and (c) a combination of about $30\times10^6$ to about $100\times10^7$ MSCs and about $2.5\times10^{11}$ to about $1\times10^{12}$ EXO-MSCs or EXO-MSC-NTFs.

In certain embodiments, the total dose of the active agent administered to the patient is selected from the group consisting of (a) about $75\times10^6$ to about $500\times10^6$ MSCs, (b) about $5\times10^{11}$ EXO-MSCs or EXO-MSC-NTFs, and (c) a combination of about $75\times10^6$ to about $500\times10^6$ MSCs and about $5\times10^{11}$ EXO-MSCs or EXO-MSC-NTFs.

In certain embodiments, the MSCs comprise bone-marrow-derived MSCs (BM-MSCs). In certain embodiments, the MSCs consist of BM-MSCs.

In certain embodiments, the therapeutically effective regime comprises repeated administration of the active agent in different months. In certain embodiments, the therapeutically effective regime comprises repeated administration of the active agent in different weeks. In certain embodiments, the therapeutically effective regime comprises repeated administration of the active agent in different days. In certain embodiments, the therapeutically effective regime comprises repeated administration of the active agent in different hours of the same day.

In certain embodiments, the repeated administration comprises administration on at least two different days. In certain embodiments, the repeated administration comprises administration on at least three different days. In certain embodiments, the repeated administration comprises administration on at least four different days. In certain embodiments, the repeated administration comprises administration on at least five different days.

In certain embodiments, the repeated administration comprises administration on consecutive days. In certain embodiments, the repeated administration comprises administration on at least two consecutive days. In certain embodiments, the repeated administration comprises administration on at least three consecutive days. In certain embodiments, the repeated administration comprises administration on at least four consecutive days. In certain embodiments, the repeated administration comprises administration on at least five consecutive days.

In certain embodiments, the repeated administration comprises administration on alternate days. In certain embodiments, the repeated administration is on day 1, day 3 and day 5. In certain embodiments, the repeated administration is on day 1, day 3, day 5, day 7 and day 9.

In certain embodiments, the pharmaceutical composition further comprises an excipient. In certain embodiments, the excipient is Plasma-Lyte A.

In certain embodiments, the volume of the pharmaceutical composition is between about 100 mL to about 120 mL. In certain embodiments, the volume of the pharmaceutical composition is 104 mL. In certain embodiments, the volume of the pharmaceutical composition is 110 mL. In certain embodiments, the volume of the pharmaceutical composition is 114 mL.

In certain embodiments, the method described above comprises systemic administration of the pharmaceutical composition. In certain embodiments, the method described above comprises intravenous administration of the pharmaceutical composition. In certain embodiments, the method described above comprises intratracheal administration of the pharmaceutical composition.

In certain embodiments, the pharmaceutical composition is fresh. In certain embodiments, the pharmaceutical composition has not been frozen. In certain embodiments, the pharmaceutical composition has been frozen. In certain embodiments, the pharmaceutical composition has been frozen and thawed. In certain embodiments, the active agent is fresh. In certain embodiments, the active agent has not been frozen. In certain embodiments, the active agent has been frozen. In certain embodiments, the active agent has been frozen and thawed.

In certain embodiments, the symptom is selected from the group consisting of pneumonia, acute respiratory distress syndrome (ARDS), multi-organ failure, fever, dry cough, fatigue, sputum production, loss of smell, shortness of breath, muscle pain, joint pain, sore throat, headache, chills, nausea, vomiting, nasal congestion, and diarrhea.

In certain embodiments, the symptom is pneumonia. In certain embodiments, the symptom is ARDS. In certain embodiments, the symptom is multi-organ failure. In certain embodiments, the symptom is fever. In certain embodiments, the symptom is dry cough. In certain embodiments, the symptom is fatigue. In certain embodiments, the symptom is sputum production. In certain embodiments, the symptom is loss of smell. In certain embodiments, the symptom is shortness of breath. In certain embodiments, the symptom is muscle pain. In certain embodiments, the symptom is joint pain. In certain embodiments, the symptom is sore throat. In certain embodiments, the symptom is headache. In certain embodiments, the symptom is chills. In certain embodiments, the symptom is nausea. In certain embodiments, the symptom is vomiting. In certain embodiments, the symptom is nasal congestion. In certain embodiments, the symptom is diarrhea.

In certain embodiments, the viral lung infection is selected from the group consisting of a Coronavirus infection, a Severe acute respiratory syndrome (SARS) infection, a Middle East respiratory syndrome (MERS) infection, an Influenza virus infection, an Ebola virus infection, a rabies infection, a West Nile virus infection, a dengue virus infection, a respiratory syncytial virus (RSV) infection, and a Zika virus infection.

In certain embodiments, the viral lung infection is a Coronavirus infection. In certain embodiments, the viral lung infection is a SARS infection. In certain embodiments, the viral lung infection is a MERS infection. In certain embodiments, the viral lung infection is an Influenza virus infection. In certain embodiments, the viral lung infection is an Ebola virus infection. In certain embodiments, the viral lung infection is a rabies infection. In certain embodiments, the viral lung infection is a West Nile virus infection. In certain embodiments, the viral lung infection is a dengue virus infection. In certain embodiments, the viral lung infection is an RSV infection. In certain embodiments, the viral lung infection is a Zika virus infection.

In certain embodiments, the active agent is selected from the group consisting of (a) MSC-NTFs, (b) EXO-MSC-NTFs, and (c) a combination of MSC-NTFs and EXO-MSC-NTFs. In certain embodiments, the active agent is MSC-NTFs. In certain embodiments, the active agent is EXO-MSC-NTFs. In certain embodiments, the active agent is a combination of MSC-NTFs and EXO-MSC-NTFs.

In certain embodiments, the active agent is a combination of MSCs and EXO-MSC-. In certain embodiments, the active agent is a combination on MSC-NTFs and EXO-MSC-NTFs.

In certain embodiments, the combination of MSC-NTFs and EXO-MSC-NTFs is administered at least 4 times to the patient. In certain embodiments, the combination of MSC-NTFs and EXO-MSC-NTFs is administered at least 5 times to the patient. In certain embodiments, the combination of MSC-NTFs and EXO-MSC-NTFs is administered 2 times to the patient. In certain embodiments, the combination of MSC-NTFs and EXO-MSC-NTFs is administered 3 times to the patient. In certain embodiments, the combination of MSC-NTFs and EXO-MSC-NTFs is administered 4 times to the patient. In certain embodiments, the combination of MSC-NTFs and EXO-MSC-NTFs is administered 5 times to the patient. In certain embodiments, the combination of MSC-NTFs and EXO-MSC-NTFs is administered no more than 2 times to the patient. In certain embodiments, the combination of MSC-NTFs and EXO-MSC-NTFs is administered no more than 3 times to the patient. In certain embodiments, the combination of MSC-NTFs and EXO-MSC-NTFs is administered no more than 4 times to the patient. In certain embodiments, the combination of MSC-NTFs and EXO-MSC-NTFs is administered no more than 5 times to the patient. In certain embodiments, the combination of MSC-NTFs and EXO-MSC-NTFs is administered 1 to 5 times to the patient. In certain embodiments, the combination of MSC-NTFs and EXO-MSC-NTFs is administered 2 to 5 times to the patient. In certain embodiments, the combination of MSC-NTFs and EXO-MSC-NTFs is administered 3 to 5 times to the patient. In certain embodiments, the combination of MSC-NTFs and EXO-MSC-NTFs is administered 4 to 5 times to the patient.

In certain embodiments, the EXO-MSC-NTFs, compared to corresponding EXO-MSCs: (1) comprise substantially less of at least one protein selected from the group consisting of A1L4H1, P49747, P02452, Q7Z304, Q5VTE0, P68104, Q05639, P60903, P08123, P09619, Q15113, P15144, O43854, Q71U36, P0DPH8, P0DPH7, Q6PEY2, Q92598, P05023, and P62873, or (2) comprise substantially more of at least one protein selected from the group consisting of P02748, P08476, P08254, P05067, P15514, P07602, P20809, CON_P13645, P13645, and P01857.

In certain embodiments, the EXO-MSC-NTFs, compared to corresponding EXO-MSCs: (1) comprise substantially less of A1L4H1, P49747, P02452, Q7Z304, Q5VTE0, P68104, Q05639, P60903, P08123, P09619, Q15113, P15144, O43854, Q71U36, P0DPH8, P0DPH7, Q6PEY2, Q92598, P05023, and P62873 proteins, and (2) comprise substantially more of P02748, P08476, P08254, P05067, P15514, P07602, P20809, CON_P13645, P13645, and P01857 proteins.

In certain embodiments, the EXO-MSC-NTFs comprises: (1) 2.46 to 2.73 pg of LIF protein per μg of total proteins, (2) 5.33 to 7.48 pg of AREG protein per μg of total proteins, (3) 0.45 to 0.78 pg of HGF protein per μg of total proteins, or (4) 0.027 to 0.065 pg of TSG6 protein per μg of total proteins.

In certain embodiments, the EXO-MSC-NTFs comprises: (1) 2.46 to 2.73 pg of LIF protein per μg of total proteins, (2) 5.33 to 7.48 pg of AREG protein per μg of total proteins, (3) 0.45 to 0.78 pg of HGF protein per μg of total proteins, and (4) 0.027 to 0.065 pg of TSG6 protein per μg of total proteins.

The term "mesenchymal stem cell" "mesenchymal stromal cell", "Multipotent Stromal Cells", "MSC", or "MSCs" is used interchangeably for adult cells, which are not terminally differentiated, which can divide to yield cells that are either stem cells, or which irreversibly differentiate to give rise to cells of a mesenchymal cell lineage or transdifferentiate into cells of other non-mesodermal lineages such as the neural lineage.

The source of MSCs may be from a healthy subject or may be from a subject to be treated or may be from a donor which is immunologically matched or immunologically-unmatched with the subject to be treated. In some embodiments, the source of MSCs may be from a subject suffering from a neurodegenerative disease. In some embodiments, MSCs comprise autologous cells. In an alternative embodiment, MSCs comprise allogeneic cells. As exemplified herein, EXO-MSCs and EXO-MSC-NTFs barely express MHC-I and MHC-II molecules, which may make immunologically-matching between exosomes and human recipients redundant.

MSCs can be found in nearly all tissues and may be isolated from various tissues. Although the bone marrow (BM) is the most widely recognized source of MSCs, recent research has identified alternative sources of MSCs, including adipose tissue (AT), placenta, dental pulp, synovial membrane, peripheral blood, oral mucosa, periodontal ligament, endometrium, umbilical cord (UC), and umbilical cord blood (UCB). In fact, evidence has suggested that MSCs may be present virtually in any vascularized tissues throughout the whole body.

In some embodiments, MSCs described herein were isolated from any tissue in which they are identified. In some embodiments, the tissue from which MSC may be isolated includes, but is not limited to, bone marrow, adipose tissue, placenta, dental pulp, synovial membrane, peripheral blood, oral mucosa, periodontal ligament, endometrium, umbilical cord Wharton Jelly, and umbilical cord blood.

In certain embodiments, the MSCs are selected from the group consisting of bone marrow MSCs, adipocyte MSCs, dental pulp MSCs, placenta MSCs, synovial membrane MSCs, peripheral blood MSCs, oral mucosa MSCs, periodontal ligament MSCs, endometrium MSCs, umbilical cord Wharton Jelly MSCs, and umbilical cord blood MSCs.

The term 'extracellular vesicles' (EVs) refers to a heterogeneous population of vesicular bodies of cellular origin that derive either from the endosomal compartment (exosomes) or as a result of shedding from the plasma membrane. Extracellular vesicles (EVs) are membrane-enclosed nanoscale particles released from essentially all prokaryotic and eukaryotic cells. EVs range in diameter from near the size of the smallest physically possible unilamellar liposome (around 20-30 nanometers) to as large as 10 microns or more, although the vast majority of EVs are smaller than 200 nm. EVs according to size and synthesis route are defined Exosomes, microvesicles and apoptotic bodies. They carry a cargo of proteins, nucleic acids, lipids, metabolites, and even organelles from the parent cell. Exosomes are small EVs (ranged 30-150 nm), generated by invagination of the endosomal membrane forming intraluminal vesicles within multivesicular bodies (MVBs).

In certain embodiments, the isolated exosome population further comprises one or more neurotrophic factors (NTF) selected from the group consisting of a hepatocyte growth factor (HGF), a granulocyte stimulating factor (G-CSF), a brain-derived neurotrophic factor (BDNF), a tumor necrosis factor-inducible gene 6 protein (TSG-6; also known as TNF-stimulated gene 6 protein), a bone morphogenetic protein 2 (BMP2), and a fibroblast growth factor 2 (FGF2), and any combination thereof. In a further related aspect, the isolated exosome population further comprises one or more miRNA molecule selected from the group consisting of miRNA (miR)-3663-3p, miR-132-3p, miR-150-3p, miR-762, miR-4327, miR-3665, miR-34a-5p, miR-1915, miR-34a-39, miR-34b-5p, miR-874, miR-4281, miR-1207-5p, miR-30b-5p, miR-29b-3p, miR-199b-5p, miR-30e-5p, miR-26a-5p, and miR-4324, and any combination thereof; or wherein the isolated exosome population is devoid of one or more miRNA molecule selected from the group consisting of miR-503, miR-3659, miR-3529-3p, miR-320b, miR-1275, miR-3132, miR-320a, miR-495, miR-181b-5p, miR-222-3p, miR-424-5p, miR-4284, miR-574-5p, miR-143-3p, miR-106a-5p, miR-455-3p, miR-20a-5p, miR-145-5p, miR-324-3p, miR-130b-3p, miR-1305, and miR-140-3p, and any combination thereof; or any combination thereof.

The term "about" as used herein is meant to define a deviation of up to 10% more and less than a given number. For example, the phrase "about 10" means "9 to 11".

The above-described embodiments are intended to be examples only. Alterations, modifications and variations can be affected to the particular embodiments by those of skill in the art. The scope of the claims should not be limited by the particular embodiments set forth herein but should be construed in a manner consistent with the specification as a whole.

EXAMPLES

Example 1. Bone Marrow Collection for Isolation of Mesenchymal Stem Cells (MSCs)

The objective of this protocol was to describe the procedure for the aspiration of Donor Bone Marrow (BM) for the isolation of Mesenchymal Stem cells to be used as a treatment for patients with viral lung infections which cause severe respiratory problems, such as severe novel coronavirus pneumonia (NCP) due to COVID-19 or other viral lung infections.

The bone marrow aspiration (BMA) procedure was preceded by documentation reporting donor's test results for HIV 1 and 2, HBV, HCV, HTLV, Syphilis and COVID-19. Positive test results that would exclude a donation may include but are not limited to tests for anti-HIV-1, anti-HIV-2; Hepatitis B virus (HBV; surface and core antigen); and Hepatitis C virus (HCV) performed within one week before BM aspiration.

Human bone marrow (80-120 ml) was aspirated by a physician as per Medical Center standard procedures (under sedation, epidural or general anesthesia as applicable), bilaterally from multiple punctures of the iliac crest of the pelvic bone into 20 mL syringes prefilled with approximately 1 mL of a Heparin-containing solution (Heparin Stock Solution, USP, 350 units/mL in PlasmaLyte).

Example 2. Propagation of MSCs

The first step of the production process involves separation of Mononuclear cells (MNC) from the total bone marrow by Ficoll density gradient centrifugation.

The hMSC were enriched in-vitro (in 2-chamber CellStacks, Corning) from Mononuclear Cells (MNC) by virtue of their ability to adhere to plastic. To prevent potential risk of infection and host immune reactions, the manufacturing process was carried out in xeno-free growth medium containing 10% human Platelet lysate (PL) and designated PM. The cells were seeded in PM in 2-Chamber CellStacks (tissue culture vessels) at 37° C./5% $CO_2$ for the first 16-24 hours. At this stage, plastic-adherent MSCs are attached to the CellStack surface and non-adherent, mononuclear cells are floating in the supernatant. The PM was replaced with fresh PM (Passage 0, "P0"). During Passage 0, hMSC culture medium was replaced four up to six (6) times. After up to 15 days, the P0 MSCs were harvested and cryopreserved.

Upon harvesting Passage P0 and before cryopreservation the MSCs culture was sampled for In-Process Sterility and the MSCs were tested for identity by flow cytometry and for the presence of *Mycoplasma.*

MSCs were identified by phenotypic analyses of cell surface markers by Flow cytometry. hMSCs are characterized by expression of CD73, CD90 CD105 on the cell surface (>95% positives). To confirm the purity of the cell population and to exclude the presence of hematopoietic cell contamination, these cells should lack expression of CD14, CD34, CD45, and HLA-DR (<5%) as determined by flow cytometry. The MSCs complied with the specifications.

Eighteen Cryotubes with $15 \times 10^6$ cells/tube were cryopreserved and stored in the vapor phase of a liquid nitrogen freezer (−196° C.) that provides stable cryogenic storage. The vapor phase liquid nitrogen freezer maintains a lower temperature, even during filling and sample retrieval cycles.

After MSC P0 cryopreservation, the cells were thawed and seeded for proliferation (Passage 1, P1). Thawed hMSCs were seeded in growth media (PM) in 2-chamber CellStacks at a concentration of 1,000 cells/$cm^2$ for seven to eight (7-8) days. The growth medium (PM) was replaced every 3 to 4 days. After up to 7-8 days, the P1 cells were harvested and, optionally, cryopreserved (Passage 1).

Upon harvesting Passage 1 and before cryopreservation the MSC culture was sampled for In-Process Sterility and *Mycoplasma.*

Cryotubes with $25 \times 10^6$ cells/tube were cryopreserved and stored in the vapor phase of a liquid nitrogen freezer (−196° C.) that provides stable cryogenic storage.

After MSC P1 cryopreservation, the cells were thawed and seeded for proliferation (Passage 2, P2). Thawed hMSCs were seeded in growth media (PM) in 2-chamber CellStacks at a concentration of 1,000 cells/$cm^2$ for seven to eight (7-8) days. The growth medium (PM) was replaced every 3 to 4 days. After up to 7-8 days, the P2 cells were harvested and cryopreserved (Passage 2).

Upon harvesting Passage 2 and before cryopreservation, the MSCs culture was sampled for In-Process Sterility and *Mycoplasma.*

Cryotubes with $30 \times 10^6$ cells/tube were cryopreserved and stored in the vapor phase of a liquid nitrogen freezer (−196° C.) that provides stable cryogenic storage. Every 5 cryotubes are sufficient for manufacturing of 1 dose ($100 \times 10^6$ of cells) for 1 patient. One cryotube is sufficient for manufacturing of 1 low dose ($20 \times 10^6$ of cells) for 1 patient. Alternatively, Cryotubes with $130 \times 10^6$ cells/tube are cryopreserved and stored in the vapor phase of a liquid nitrogen freezer (−196° C.) that provides stable cryogenic storage.

For patient treatment with allogeneic MSCs, the cells were thawed, and final product was prepared. Upon MSCs thawing, the cells were pooled, washed and counted. MSCs were then loaded in a syringe and labelled. The MSCs suspension was sampled for final bulk safety tests: Sterility, Gram staining, Endotoxins. Alternatively, cells from a cryotube with $130 \times 10^6$ cells/tube will be thawed by the patient bed and will immediately be injected to the patient.

The final product syringe was tested for appearance (visual inspection) and was found to comply with specifications (intact syringe, cloudy and yellowish cell suspension and practically free from visible particulates).

Example 3. Production, Purification, and Characterization of EXO-MSCS, Including EXO-MSC-NTFS For scaling-up exosomes manufacturing and yield, thawed MSCs (P0 or P1; see example 2) were resuspended in PM medium, and either seeded directly in the Quantum Cell Expansion system bioreactor (Terumo BCT) or seeded in CellStacks for several days propagation in order to be re-seeded in a PBS bioreactor system (PBS Biotech).

Quantum.

The Quantum Cell Expansion system is a functionally closed, automated hollow fiber bioreactor system. The bioreactor itself is comprised of ~11,500 hollow fibers with a total intracapillary (IC) surface area of 2.1 $m^2$. The Quantum system fluid circuit is designed around two fluid loops: one loop for the IC and one for the extra-capillary (EC) part of the hollow-fibers.

The PBS bioreactor system (PBS Biotech) is a vertical wheel single-use bioreactor that can provide homogeneous, low-shear, and scalable mixing across a wide range of working volumes.

Bioreactor Cell Culture for Exosomes.

The first step of the production process involves separation of Mononuclear cells (MNCs) from the total bone marrow by Sepax 2 (Cytiva) that is a fully automated closed and compact solution to process separation of MNC by Ficoll density gradient centrifugation. The Quantum Cell Expansion system was seeded either with MNCs after Sepax separation or with thawed P0, or P1 MSCs that had been propagated in CellStacks.

Prior to cells seeding, the bioreactor was coated for at least 4 hours to overnight with 5 to 10 mg of fibronectin to promote cell adhesion using the 'Coat Bioreactor Task'. After the 4 hours to overnight bioreactor coating, any excess fibronectin was washed from the bioreactor set and the cell culture media was introduced into the set utilizing the IC/EC Washout Task allowing the exchange of PBS solution with PM growth media in DMEM with no additional antibiotics/antimycotics.

The human MSCs (hMSCs) were enriched in-vitro in the Quantum system bioreactor from Mononuclear Cells (MNCs) by virtue of their ability to adhere to the surface of the hollow fiber. To prevent potential risk of infection and host immune reactions, the manufacturing process was carried out in xeno-free growth medium containing 10% human Platelet lysate (PL with no additional antibiotics/antimycotics) and is designated PM. The cells were seeded in PM in the Quantum system at 37° C./5% $CO_2$ for the first 16-24 hours. At this stage, hollow fiber-adherent MSCs were attached to the surface and non-adherent, mononuclear cells were floating in the supernatant. The PM was replaced with fresh PM (Passage 0, "P0"). After up to 15 days, the P0 MSCs were harvested and one part was cryopreserved (Passage 0) and a 2nd part was reseeded in a new Quantum Cell Expansion system bioreactor.

Twenty million Passage 0 MSCs, were transferred into the Cell Inlet Bag of the Quantum system bioreactor and the total volume of the bag was brought up to 100 mL with PM. The bag was then sterile-connected to the Cell Inlet Line of the Quantum system and cells were loaded into the fibronectin precoated IC side of the bioreactor utilizing the 'Load Cells with Circulation' task. Cells were propagated for 6-7 days utilizing the 'Feed Cells' task with the fresh PM added to the IC side of the bioreactor and the IC inlet rate adjusted as required by the rate of glucose consumption and lactate generation in the system as sampled from the Sample Port daily. After 6-7 days the MSCs (Passage 1, "P1") were harvested.

Upon harvesting Passage P1 and before cryopreservation the MSCs culture was sampled for In-Process Sterility and the MSCs were tested for identity by flow cytometry and for the presence of *Mycoplasma*.

MSCs are identified by phenotypic analyses of cell surface markers by Flow cytometry. hMSCs are characterized by expression of CD73, CD90 CD105 on the cell surface. To confirm the purity of the cell population and to exclude the presence of hematopoietic cell contamination, these cells should lack expression of CD14, CD34, CD45, and HLA-DR as determined by flow cytometry.

Cryotubes with $15\times10^6$ cells/ml were cryopreserved and stored in the vapor phase of a liquid nitrogen freezer (−196° C.) that provides stable cryogenic storage. The vapor phase liquid nitrogen freezer maintains a lower temperature, even during filling and sample retrieval cycles.

After MSCs P1 cryopreservation, the cells were thawed and seeded for proliferation (Passage 2, P2). Twenty million thawed and washed MSCs (cells were frozen and cryopreserved in liquid $N_2$ at Passages 0-2) were transferred into the Cell Inlet Bag and the total volume of the bag was brought up to 100 mL with PM. The bag was then sterile-connected to the Cell Inlet Line of the Quantum system and cells loaded into the fibronectin precoated IC side of the bioreactor utilizing the 'Load Cells with Circulation' Task. Cells were propagated for 6-7 days utilizing the Feed Cells Task with the fresh PM added to the IC side of the bioreactor and the IC inlet rate adjusted as required by the rate of glucose consumption and lactate generation in the system as sampled from the Sample Port daily. After 6-7 days the medium was replaced with platelet lysate free medium. Cell culture medium containing exosomes was collected every 48 h for a total of 2-5 times in order to produce the maximal number of exosomes from the same cells, in consideration of the rate of glucose consumption and lactate generation.

PBS3 MAG. A PBS3 MAG bioreactor equipped with a 3 liters single use vessel (PBS biotech) was loaded with 100-200 grams of Synthemax II low-concentration microcarriers (Corning), or with enhanced attachment microcarriers (Corning). The vessel was then filled with 1.8 L of cell culture medium (DMEM high glucose supplemented with 1-2% human platelet lysate, glutamine, Pyruvate, 200 uM ascorbic acid and Heparin) and allowed to equilibrate overnight.

70-80*10^6 MSCs were inoculated into the single use bioreactor vessel, allowed to attach to the microcarriers for 20-60 min during the attachment phase, before initiating the agitation of the wheel impeller at low speed for 4-6 hours. After the attachment phase the agitation speed of the wheel impeller was increased, and an additional 1.2 L of cell culture medium was added to the vessel to make up a total volume of 3 L and a final concentration of human platelet lysate of 10%.

EXO-MSC were generated by culturing MSC under continuous agitation for 5-7 days, performing 50-80% medium exchanges every day starting on day 3 while maintaining the final concentration of PL at 10%. On the last day of culture, the medium was exchanged to platelet lysate free medium in order to collect exosomes. Cell culture medium containing exosomes was collected at the end of the process, alternatively it can be collected every 48 h for a total of 2-5 times.

After the collection, all collected medium was pooled together for exosome isolation.

EXO-MSC-NTFs were generated by culturing cells under continuous agitation for 5-7 days, performing 50-80% medium exchanges every day starting on day 3 while maintaining the final concentration of PL at 10%. On the last day of culture, the growth medium was replaced with S2M differentiation medium (Dulbecco's Modified Eagle's Medium high glucose (Sigma, Aldrich), comprising 1 mM dibutyryl cyclic AMP (cAMP), 20 ng/ml human Basic Fibroblast Growth Factor (hBFGF), 5 ng/ml human platelet derived growth factor (PDGF-AA), and 50 ng/ml human Heregulin β1 and supplemented with 200 uM Ascorbic Acid) for the collection of exosomes after 72 hours. Exosomes isolation steps are described below and are the same for EXO-MSCs and EXO-MSC-NTFs. Tangential Flow Filtration (TFF) was used to isolate and purify EXO-MSC and EXO-MSC-NTFs. Exosomes containing medium was first passed through a 100 μm separation bag in order to remove microcarriers, then the medium was filtered with a 0.8-1.2μ filter to remove cell debris. The exosome containing filtrate was collected under sterile conditions and subjected to Tangential Flow Filtration (TFF) (Repligen).

TFF—by either 100, 300, or 500-kDa (Molecular Weight Cut Off (MWCO) membranes with filtration areas of 500-1000 $cm^2$ or 2,500-5,000 $cm^2$ were used (Repligen). The exosome-containing sample was continuously pumped through the membrane system and recirculated. Small molecules, including free proteins not included within or associated with the membrane vesicles, were driven through the membrane pores, subsequently eluted as permeate, and eventually discarded. Molecules too large to pass through the pores, such as exosomes (or larger microvesicles), were kept in circulation as retentate. The sample was subjected to five to ten diafiltration volumes, in order to further deplete the sample of contaminants smaller than the kDa MWCO membrane. During the last cycle of diafiltration, the sample was reduced to a volume of ~100 ml. Finally, the sample was sterile filtered through a 0.2 μm filter.

Nanoparticle Tracking Analysis. Amount and size of particles were measured using a ZetaView Nanoparticle Tracking Analyzer (ParticleMetrix), a laser scattering video microscope tracking the movement of individual nanoparticles under Brownian motion. Five exposures at 11 measurement positions were recorded for each sample. Particle size was calculated according to the Stokes-Einstein equation by the ZetaView software (ZetaView 8.02.28).

FACS analysis. Phenotypic examination of exosomes was performed by the MACSPlex exosome kit which allows detection of 37 exosomal surface epitopes as well as two isotype controls. This Kit comprises a cocktail of various fluorescently labeled bead populations, each coated with a specific antibody binding the respective surface epitope. The 39 bead populations can be distinguished by different fluorescence intensities detected in the FITC and PE channels of the flow cytometer. Analysis of exosomes derived from BM-MSC revealed high expression of tetraspanins (conserved set of proteins expressed on exosomes, which include CD81, CD63, and CD9), MSC CD markers (CD44, CD29, CD49e) and were negative for hematopoietic CD markers (such as CD4, CD19) and HLA-DR and HLA-ABC.

Example 4. Evaluation of the Efficacy of EXO-MSCs Treatment in ARDS Mice Model The objective of this study was to explore the effectiveness of bone marrow derived mesenchymal stem cell exosomes (via intratracheal or IV administration) in a mouse model of acute respiratory distress syndrome (ARDS), the main cause for Corona virus mortality.

Use of animals in ARDS models enables to test the efficacy of EXO-MSCs in the inhibition of clinical symptoms, caused by the inflammatory response, and enables development of this treatment for ARDS. The LPS-induced ARDS model is an accepted model for severe human acute respiratory disease caused by the Corona virus infection.

Dosing was performed by administration of EXO-MSCs via endotracheal tube (intratracheal) or IV administration of EXO-MSCs at a concentration of $2.0\times10^{10}$ vesicles/1 ml (Table 1).

Animals. Animal model selection: LPS-induced ARDS. Species/Strain: BALB/C mice. Gender/Number/Age: Female, n=60, 8 weeks old.

TABLE 1

Group Designation.

| Group number | Experimental group | N | Treatment | Treatment frequency | ROA |
|---|---|---|---|---|---|
| 1 | LPS | 10 | Plasmalyte | Daily (20 ul on the first day and 50 ul in the next 2 days) | Intratracheal |
| 2 | LPS | 10 | EXO-MSC (Quantum) | Daily (20 ul in the first day and 50 ul in the next 2 days) | Intra-tracheal |
| 3 | LPS | 10 | EXO-MSC (Q) | Daily (300 ul) | IV |
| 4 | LPS | 10 | EXO-MSC (PBS) | Daily (300 ul) | IV |
| 5 | LPS | 10 | Plasmalyte | Daily (300 ul) | IV |
| 6 | Control (without LPS instillation) | 10 | Plasmalyte | Daily (300 ul) | IV |

Induction of ARDS: BALB/c mice were anaesthetized and orally intubated with a sterile plastic catheter and challenged with intratracheal instillation of 800 μg of LPS dissolved in 50 μL of normal PBS. Naive mice (without LPS instillation, study group 6) were injected with the same volume of pyrogen-free PBS to serve as controls.

Treatment: Daily administration of EXO-MSCs via endotracheal tube or IV administration at a concentration of $2.0\times10^{10}$ vesicles/1 ml. Treatment started 3 hours after LPS administration.

Sample collection: bleeding for full blood hematology for cell counts and serum analyses. Determination of total Bronchial Alveolar Lavage (BAL) and differential cell count by FACS, for: T and B lymphocytes, eosinophils, neutrophils, dendritic cells and monocytes/macrophages was performed. BAL fluid samples were also analyzed for the presence of inflammatory cytokines. Lungs were isolated from all animals sacrificed on day 3, for Histopathology H&E.

Histological evaluation. A quantitative analysis for Acute Lung Injury (ALI) was performed using a severity scoring scale of 0-2, based on the American Thoracic Society Acute Lung Injury in Animals Study Group (Matute-Bello et al., Am J Respir Cell Mol Biol 44; 725-738, 2011, incorporated herein by reference).

1. Neutrophils: Not visible within the field—a score of 0; 1-5 neutrophils—1; More than 5 neutrophils—2. 2. Fibrin: Not visible within the field—a score of 0; A single well-formed band of fibrin within the airspace—1; Multiple eosinophilic membranes—2. Thickened alveolar walls: Due to technical artifacts, only septal thickening that is equal or greater than twice normal was considered. Less than x2—score 0; x2-x4—1; More than x4—2.

FIG. 1 shows lung histopathology results of representative mice from Groups 1-6 (see Table 1).

Figure 2A:
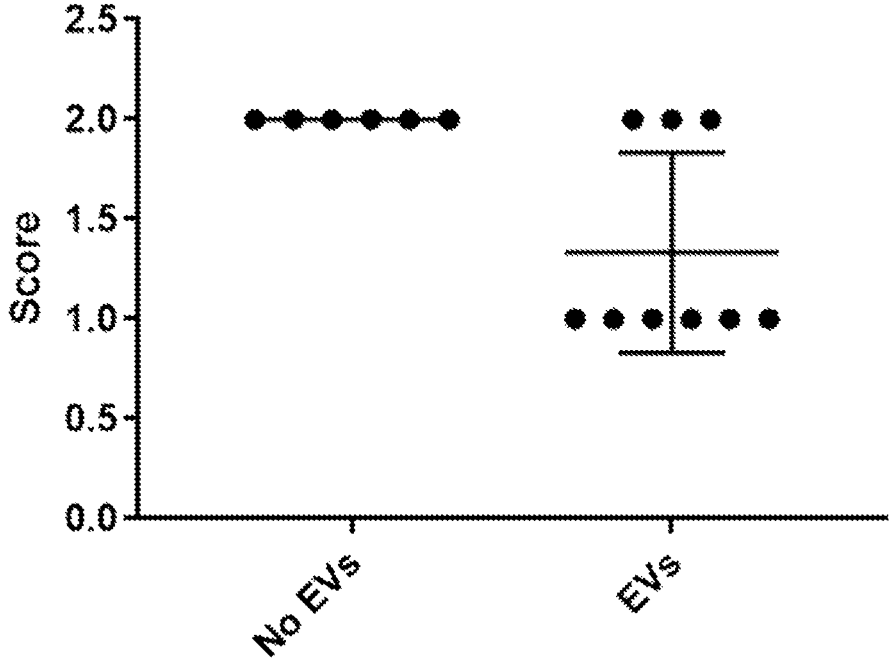
FIG. 2. Thickened alveolar wall score (FIG. 2A) and intratracheal total score (FIG. 2B). EVs=EXO-MSCs.
Figure 2B:
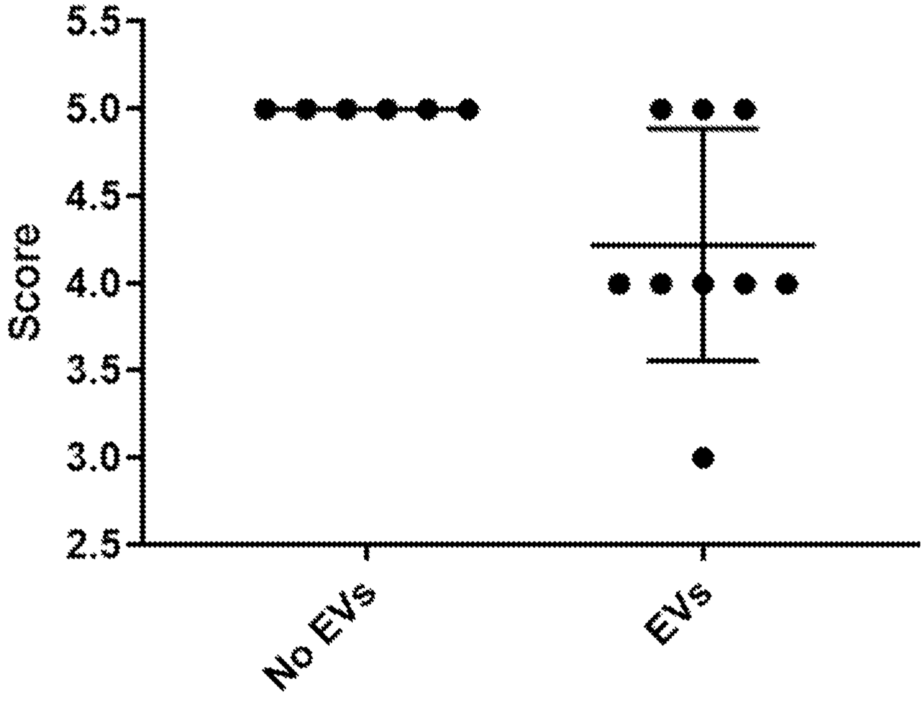
Figure 3A:
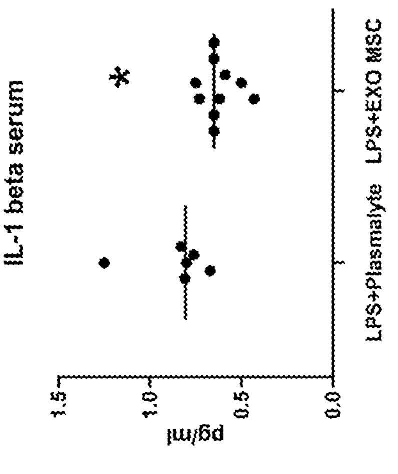
FIG. 3. Cytokine serum levels. IL-1 beta serum (FIG. 3A), IL-6 serum (FIG. 3B), MCP-1 serum (FIG. 3C), IFN gamma serum (FIG. 3D) and TNF alpha serum (FIG. 3E)
Figure 3B:
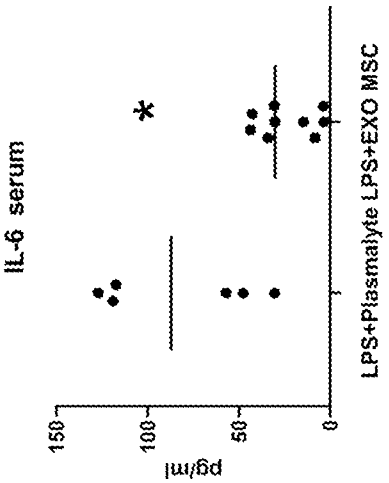
Figure 3C:
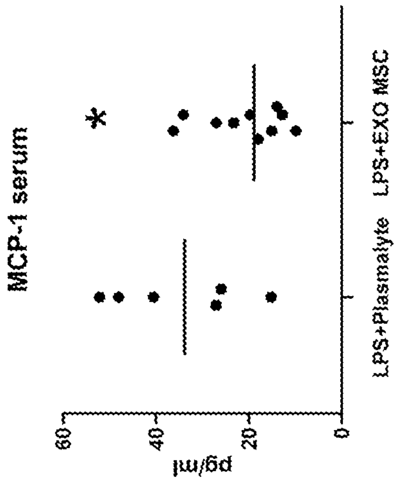
Figure 3D:
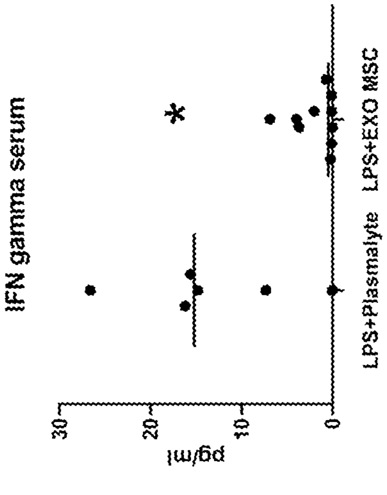
Figure 3E:
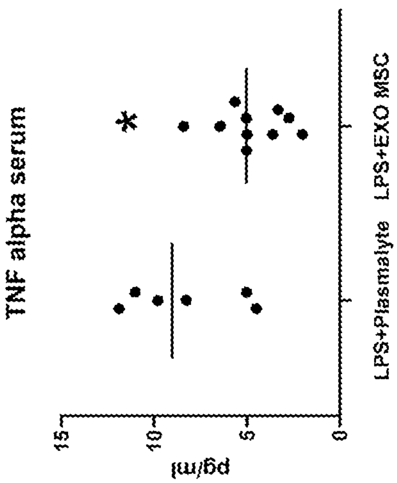
Figure 4B:
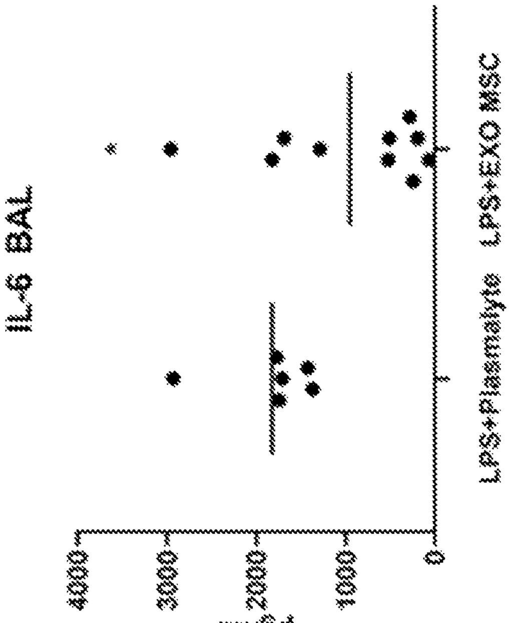
FIG. 4. Cytokine lung fluid (Broncho Alveolar fluid, BAL) levels. IL-1 beta BAL (FIG. 4A), IL-6 BAL (FIG. 4B), IP-10 BAL (FIG. 4C), IFN gamma BAL (FIG. 4D), TNF alpha BAL (FIG. 4E), MCP-1 BAL (FIG. 4F), IL-1 alpha BAL (FIG. 4G). $*p \leq 0.05$; $p \leq 0.01$; $*p \leq 0.001$.
Figure 4A:
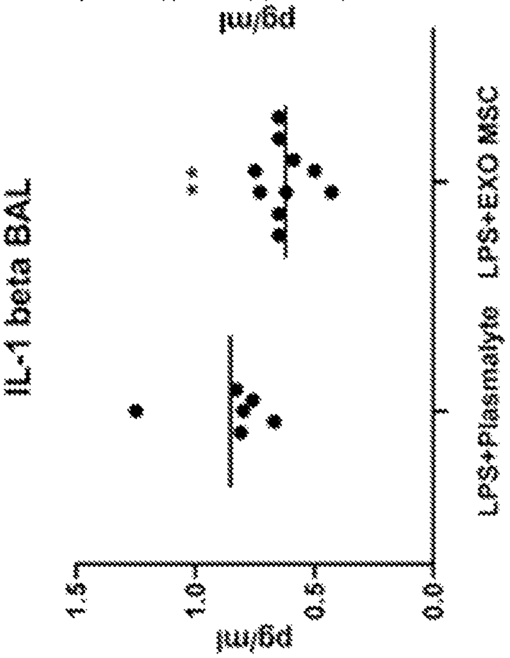
Figure 4C:
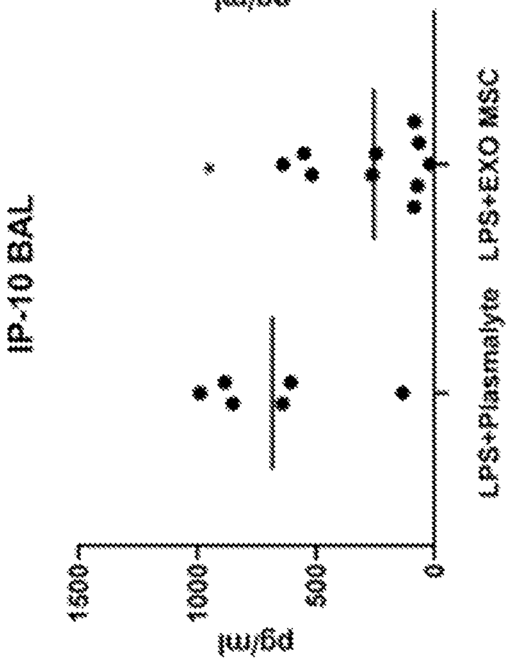
Figure 4D:
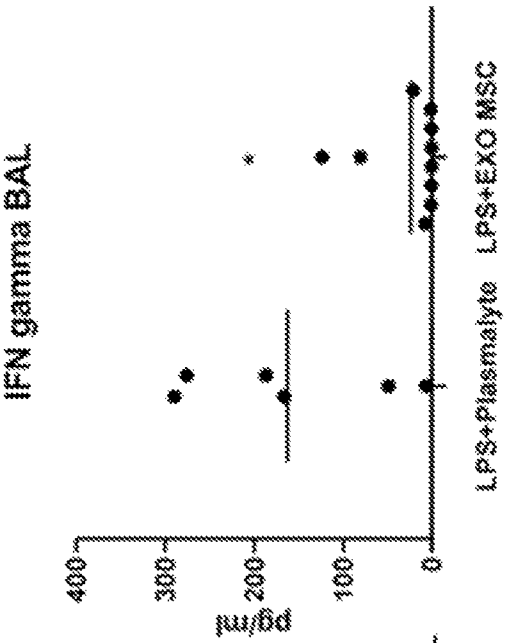
Figure 4F:
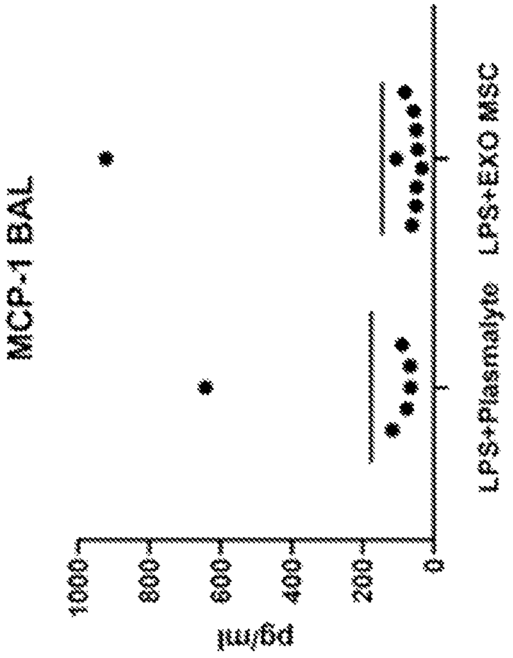
Figure 4E:
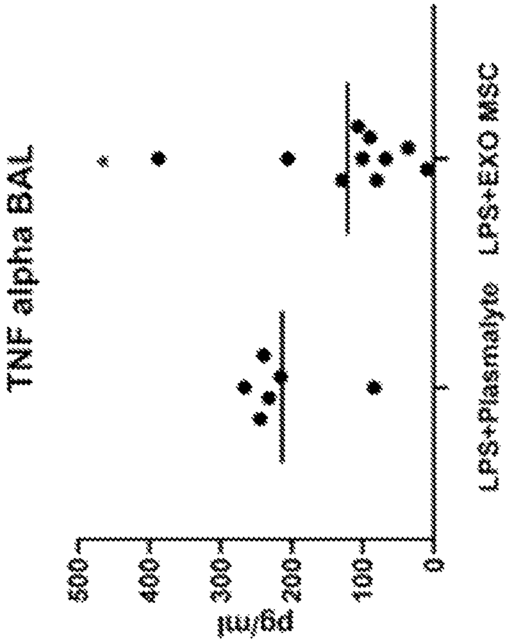
Figure 4G:
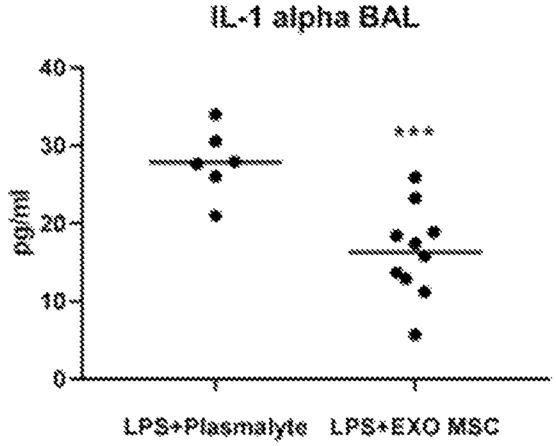

FIG. 2 shows histopathology-based group scores for thickened alveolar wall for intratracheal administration of exosomes for Groups 1 ("No EVs"="LPS+PlasmaLyte") and 2 (EVs=EXO-MSCs) (FIG. 2A). A statistically significant difference is demonstrated, indicating that exosome therapy was effective in reducing alveolar wall thickening. FIG. 2B further shows histopathology-based total Acute Lung Injury scores for intratracheal administration of exosomes for Groups 1 ("No EVs="LPS+PlasmaLyte") and 2 (EVs=EXO-MSCs). A statistically significant difference was demonstrated, indicating that exosome therapy was effective.

FIG. 3 shows serum levels of IL-1-beta (FIG. 3A), IL-6 (FIG. 3B), MCP-1 (FIG. 3C), IFN-gamma (FIG. 3D), and TNF alpha (FIG. 3E), and of mice treated with intratracheal EXO-MSCs vs mice treated with PlasmaLyte. A statistically significant difference was demonstrated (*$p<0.05$), indicating that exosome therapy was effective in reducing cytokine serum levels.

FIG. 4 shows lung fluid levels of IL-1-beta (FIG. 4A), IL-6 (FIG. 4B), IP-10 (FIG. 4C), IFN-gamma (FIG. 4D), TNF alpha (FIG. 4E), MCP-1 (FIG. 4F), and IL-1-alpha (FIG. 4G) of mice treated with intratracheal EXO-MSCs vs mice treated with PlasmaLyte. A statistically significant difference was demonstrated, indicating that exosome therapy was effective in reducing cytokine lung fluid levels.

Figure 5:
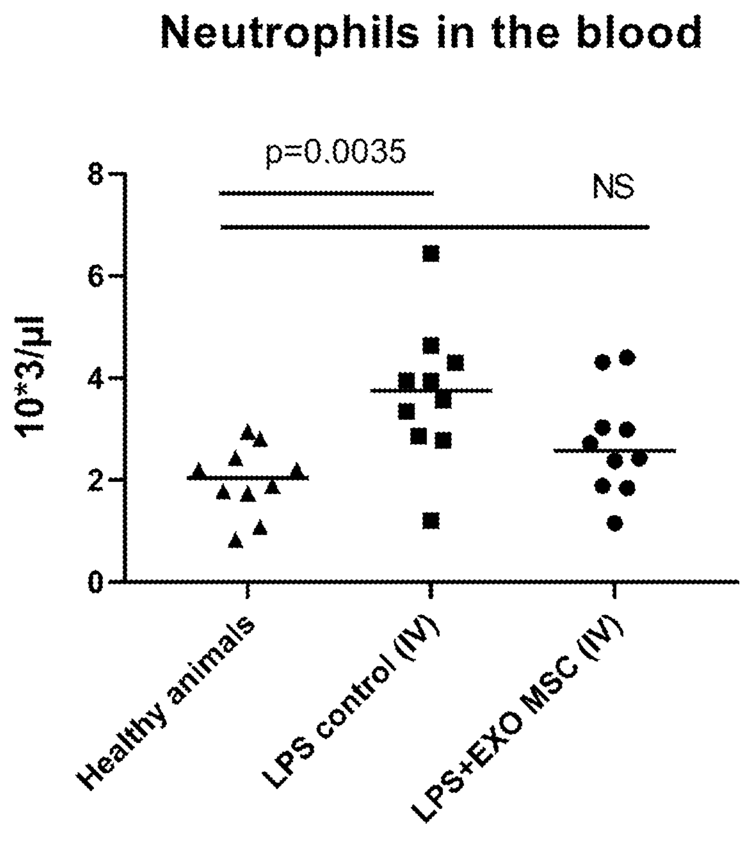
FIG. 5. Neutrophil blood levels.

FIG. 5 shows blood levels of neutrophils of healthy animals (Controls), LPS control, and LPS+EXO-MSC-IV treated mice. A statistically significant increase in blood neutrophils was observed in the LPS control while EXO-MSC treatment attenuated the effect of LPS.

Example 5. Murine Model of LPS-Induced Acute Lung Injury

The objective of this study was to explore the effectiveness of bone marrow derived mesenchymal stem cell or EXO-MSC-NTFs (via intratracheal administration) in a mouse model of ARDS, the main cause for Corona virus mortality. The LPS-induced ARDS model is an accepted model for severe human acute respiratory disease caused by Corona virus infection.

Dosing was performed by daily administration via endotracheal tube of MSC or EXO-MSC-NTFs at a concentration of $2.0\times10^{10}$ vesicles/1 ml (see Table 2).

Induction of ARDS: BALB/c mice were anaesthetized and orally intubated with a sterile plastic catheter and challenged with intratracheal instillation of 800 μg of LPS for groups 1, 2, 3 dissolved in 50 μL of normal PBS. Naive mice (without LPS instillation, study group 4) were injected with the same volume of pyrogen-free PBS to serve as controls.

Treatments: Daily administration via endotracheal tube of EXO-MSC or EXO-MSC-NTFs at a concentration of $2.0\times10^{10}$ vesicles/1 ml. Treatment started 3 hours after LPS administration.

TABLE 2

Group Designation.

| Group number | Experimental group | N | Treatment | Treatment frequency | Study duration | ROA |
|---|---|---|---|---|---|---|
| 1 | LPS | 10 | EXO-MSC | Daily (50 ul) | 72 hr | Intratracheal |
| 2 | LPS | 10 | EXO-MSC-NTF | Daily (50 ul) | 72 hr | Intratracheal |
| 3 | LPS | 15 | None (Plasmalyte) | Daily (50 ul) | 72 hr | Intratracheal |
| 4 | Control (without LPS instillation) | 10 | None (Plasmalyte) | Daily (50 ul) | 72 hr | Intratracheal |

Figure 6:
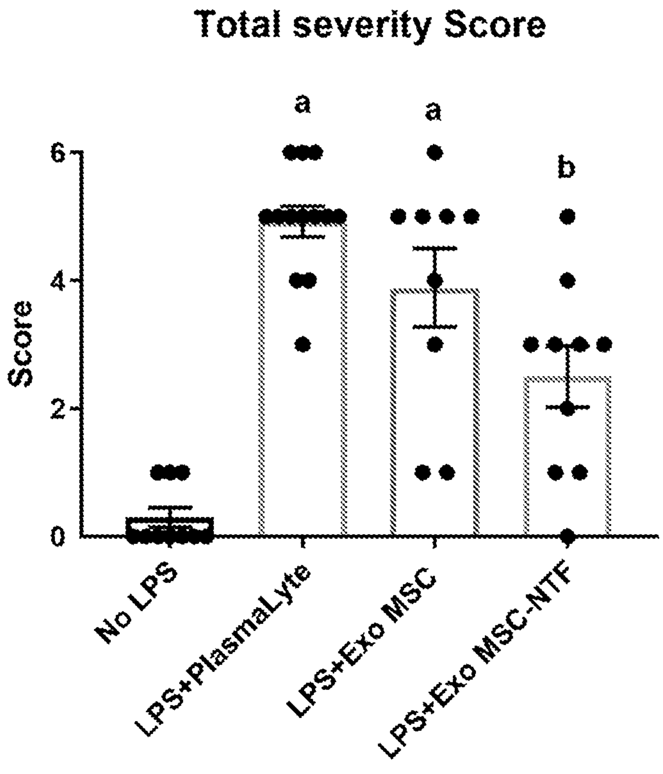
FIG. 6. Total Acute Lung Injury severity score by intratracheal administration. $^{a}$ $p \leq 0.05$ vs. no LPS control; $^{b}$ $p<0.05$ vs. LPS+PlasmaLyte.

FIG. 6 depicts the Total Acute Lung Injury severity score for groups 1-4. As can be seen, treatment with EXO-MSC-NTFs significantly protected mice from the effect of LPS.

FIG. 7 depicts the scores of fibrin (FIG. 7A), alveolar wall thickness (FIG. 7B), and neutrophils (FIG. 7C), for groups 1-4. As can be seen, treatment with EXO-MSC-NTFs significantly reduced the effect of LPS on fibrin and alveolar wall thickness.

Figure 7A:
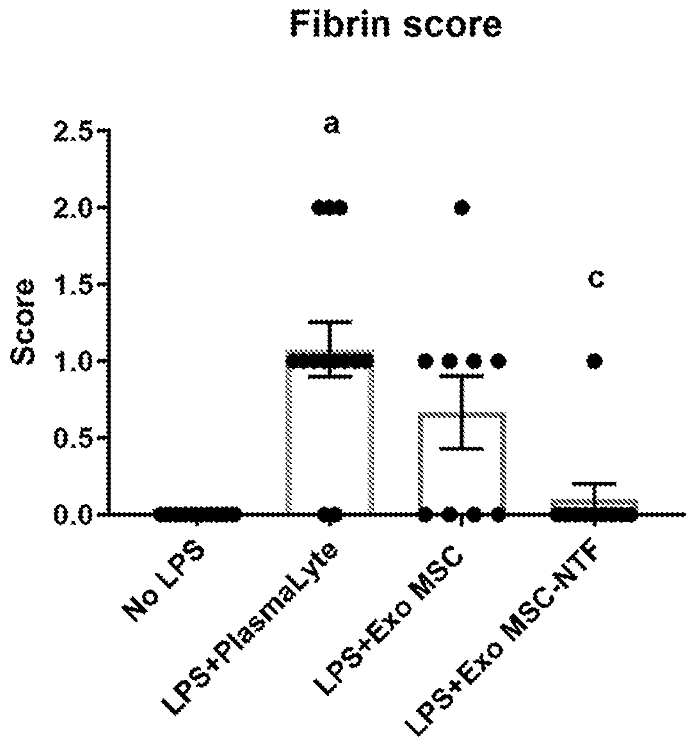
FIG. 7A. Fibrin deposition score $^{a}$ $p<0.05$ vs. no LPS control; $^{c}$ $p \leq 0.01$ vs. LPS+PlasmaLyte.
Figure 7B:
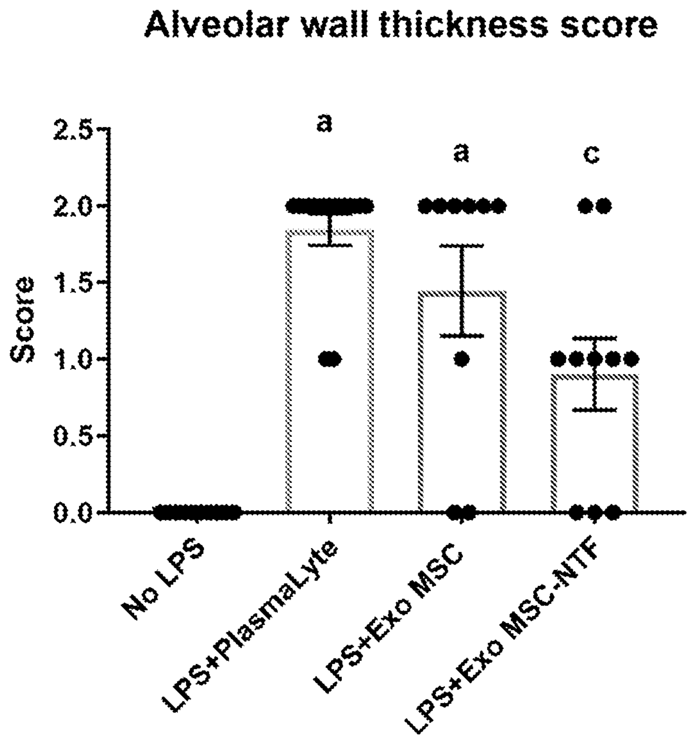
FIG. 7B—Alveolar wall thickness score $^{a}$ $p<0.05$ vs. no LPS control; $^{c}$ $p \leq 0.01$ vs. LPS+PlasmaLyte.
Figure 7C:
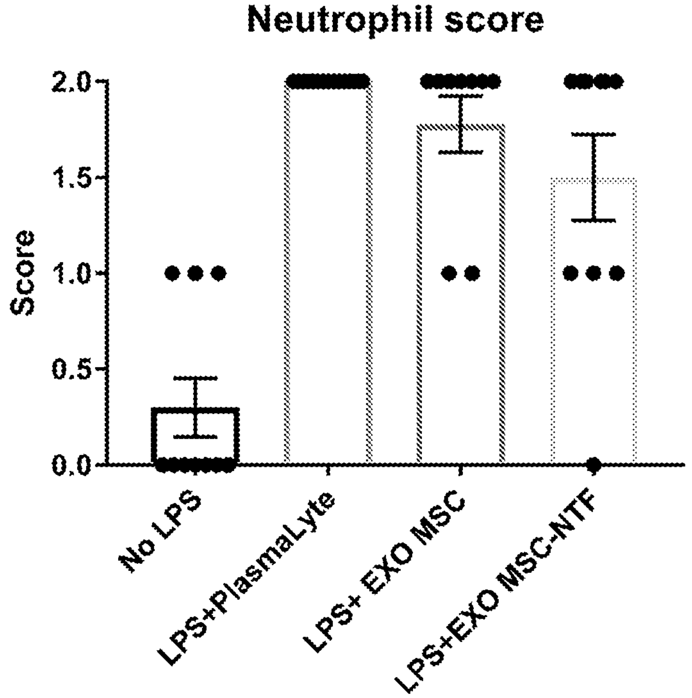
FIG. 7C—Neutrophil score.
Figure 7D:
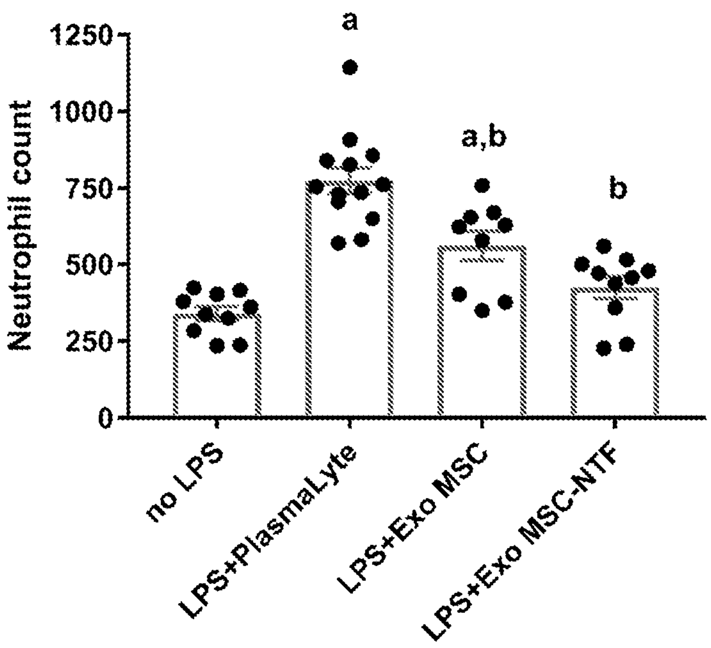
FIG. 7D. Neutrophil count in lung sections $^{a}$ $p<0.05$ vs. no LPS control; $^{b}$ $p<0.05$ vs. LPS+PlasmaLyte.
Figure 8A:
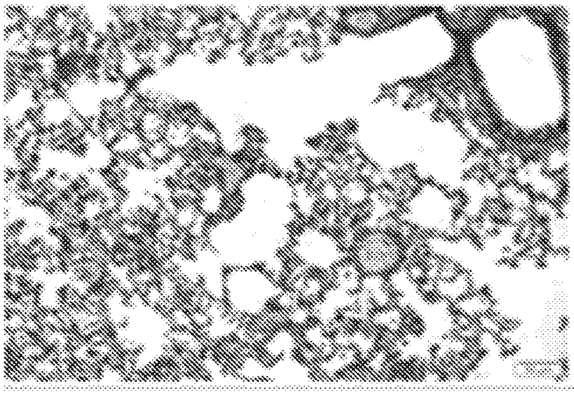
FIG. 8A—moderate affected lung—LPS EXO-MSCs.
Figure 8B:
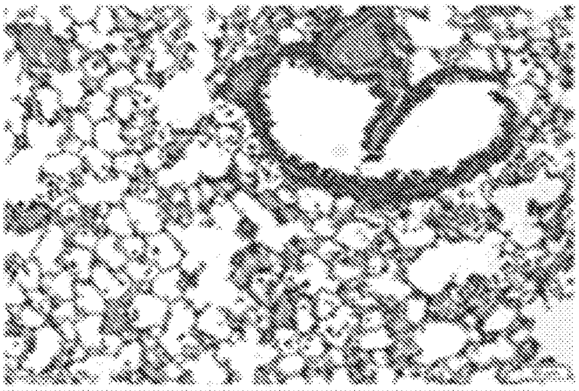
FIG. 8B—moderate affected lung—LPS EXO-MSC-NTFs.
Figure 8C:
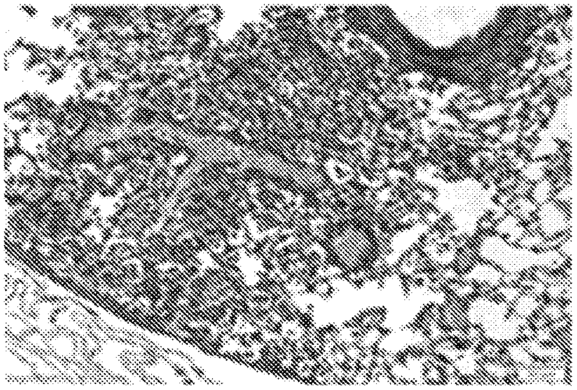
FIG. 8C—moderate to severe affected lung—LPS control (PlasmaLyte).
Figure 8D:
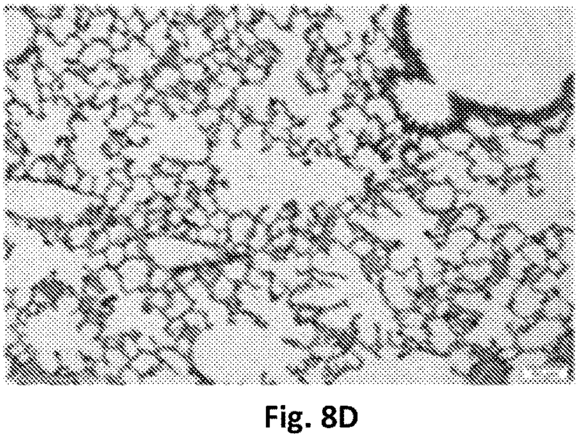
FIG. 8D—unaffected lung-healthy control (PlasmaLyte)

FIG. 7 additionally depicts neutrophil count in lung sections for groups 1-4 (FIG. 7D). As can be seen, treatment with EXO-MSC-NTFs significantly reduced the number of infiltrating neutrophils in the lungs following LPS administration. Moreover, the number of neutrophils following EXO-MSC-NTFs treatment was not significantly different from the number of neutrophils in mice that did not receive LPS.

FIG. 8—Histopathology: Perivascular infiltration of mainly neutrophils (acute) in a multi focal distribution is shown. Fibrin deposition is mild, and the alveolar walls are thickened in the affected areas. Group 3 (FIG. 8C) showed a moderate to severe lung injury with resp. 4.4 in average. Groups 1 (FIG. 8A) and 2 (FIG. 8B) showed a moderate lung injury with 3.6 and 2.5 respectively. Group 4 (FIG. 8D) showed extremely low score with a group average of resp. 0.3.

Figure 9:
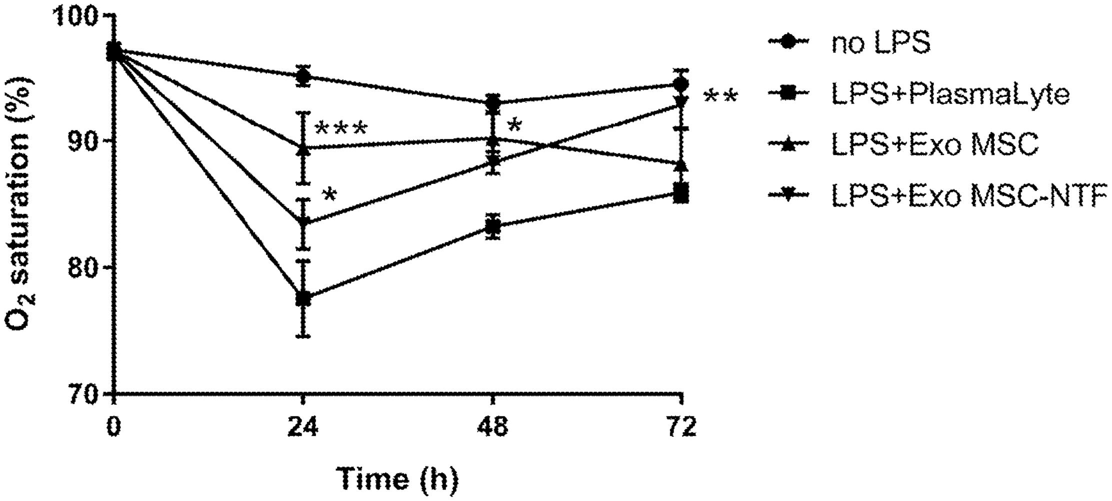
FIG. 9. Oxygen saturation (%). $*p<0.05$, $p<0.01$, $*p<0.001$ vs. the LPS+PlasmaLyte group.

FIG. 9 depicts the oxygen saturation for groups 1-4. As can be seen, treatment with EXO-MSC-NTFs or with EXO-MSCs significantly decreased the effect of LPS.

Figure 10A:
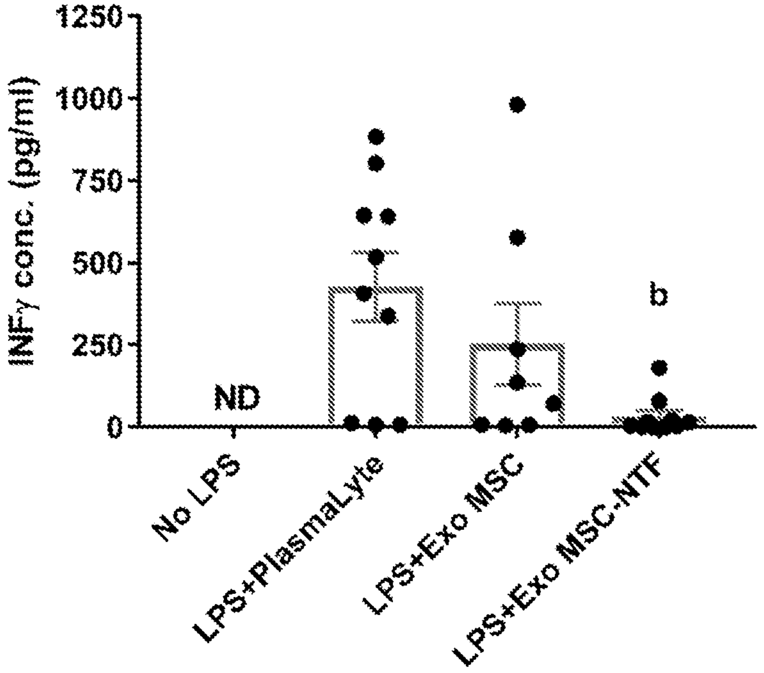
FIG. 10A—IFN-gamma levels $^{b}$ $p<0.05$ vs. LPS+PlasmaLyte.
Figure 10B:
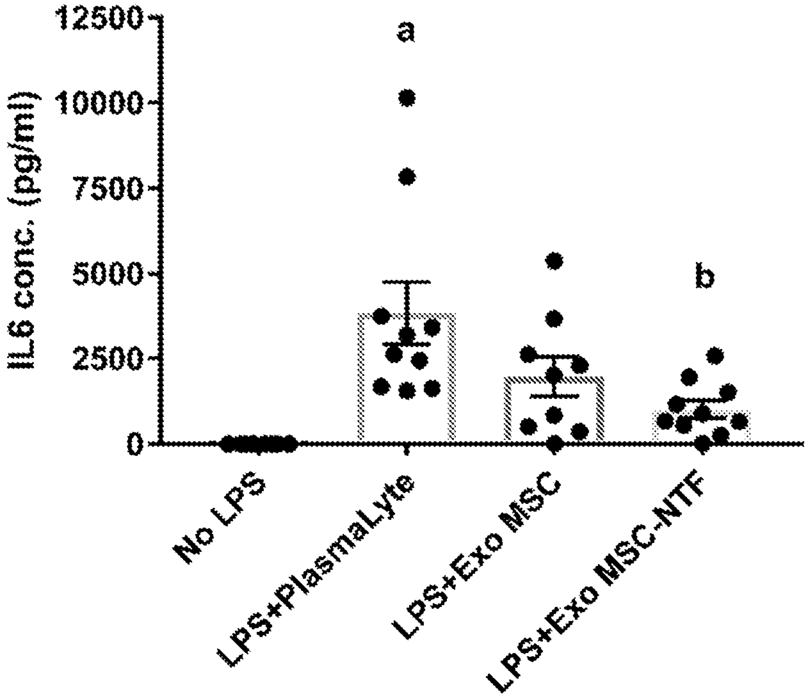
FIG. 10B—IL-6 levels $^{a}$ $p<0.05$ vs. no LPS control, $^{b}$ $p<0.05$ vs. LPS+PlasmaLyte.

FIG. 10 depicts the BAL fluid concentrations of IFN-gamma (FIG. 10A) and IL-6 (FIG. 10B) for groups 1-4. As can be seen, treatment with EXO-MSC-NTFs significantly decreased the effect of LPS on IFN-gamma and IL-6 levels.

Figure 11A:
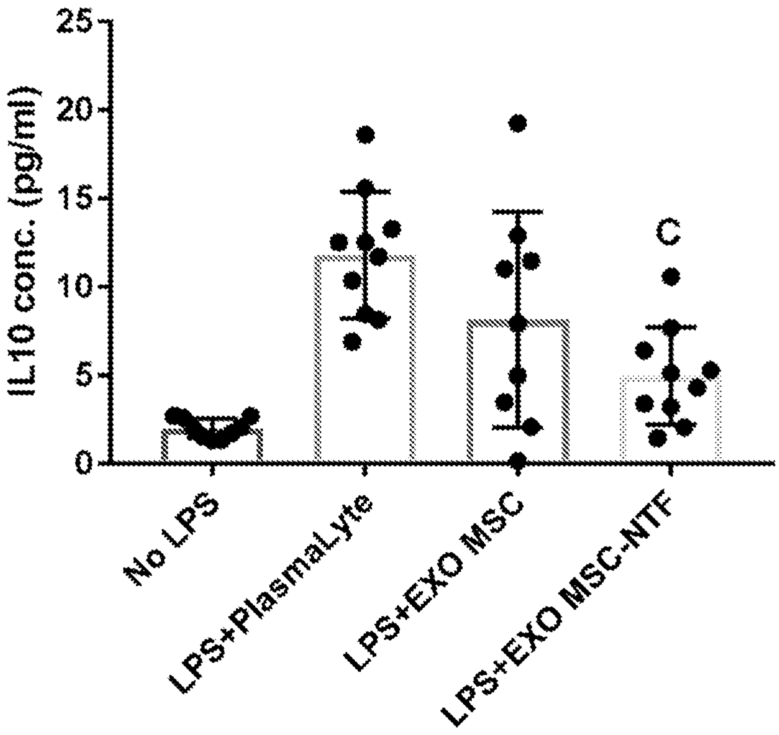
FIG. 11A—IL-10 levels $^{c}$ $p \leq 0.01$ vs. LPS+PlasmaLyte.
Figure 11B:
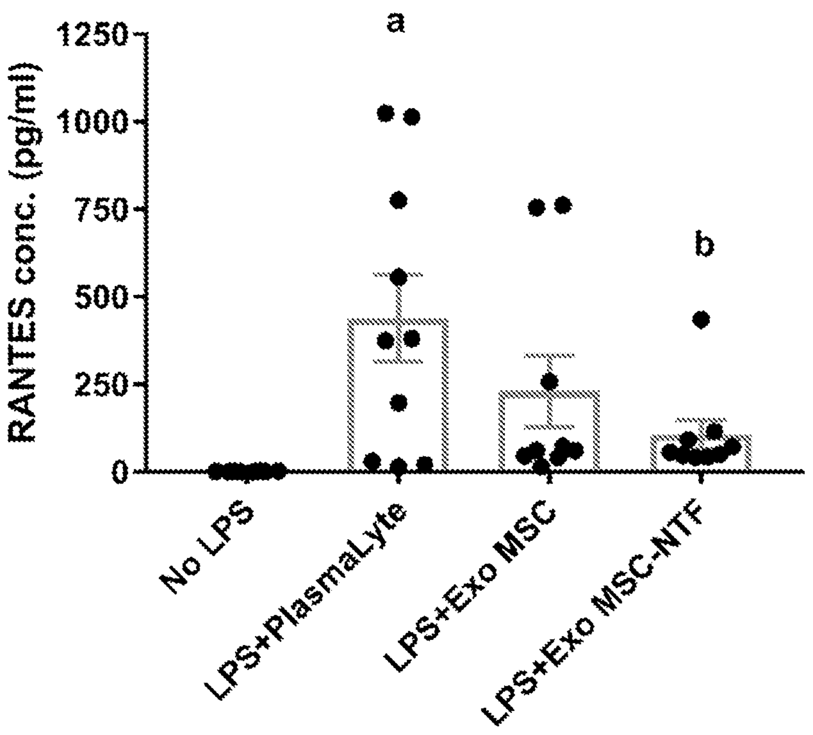
FIG. 11B—RANTES levels. $^{a}$ $p<0.05$ vs. no LPS control, $^{b}$ $p<0.05$ vs. LPS+PlasmaLyte.

FIG. 11 depicts the BAL fluid concentrations of IL-10 (FIG. 11A) and RANTES (FIG. 11B) for groups 1-4. As can be seen, treatment with EXO-MSC-NTFs significantly decreased the effect of LPS on IL-10 and RANTES levels.

Figure 12:
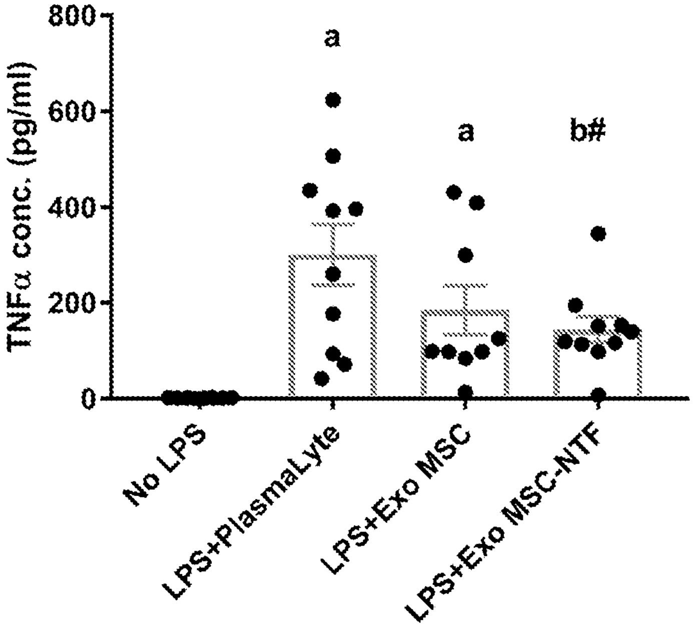
FIG. 12. Broncho Alveolar fluid cytokine levels: TNF-alpha levels. $^{a}$ $p<0.05$ vs. no LPS control, $^{b}$ $p<0.05$ vs. LPS+PlasmaLyte, $^{b\#}$ $p=0.058$ vs. LPS+PlasmaLyte.

FIG. 12 depicts the BAL fluid concentrations of TNF-alpha for groups 1-4. As can be seen, treatment with EXO-MSC-NTFs significantly decreased the effect of LPS on TNF-alpha level.

Severe forms of COVID-19 are related to thrombotic coagulopathy. Its pathogenesis involves the effect of the virus on the immune system and the downregulation of ACE2 that causes an increase in angiotensin II levels. Both pro-inflammatory cytokines and increased angiotensin II are known factors for the induction of Tissue factor (TF), as well as activated neutrophils. TF may be a critical mediator associated with the development of thrombotic phenomena in COVID-19.

Another coagulation factor, Thrombin-antithrombin complex (TAT) was found to be higher in non-survivors than in survivors during the early and middle stage of the disease, reflected by an excess generation of thrombin. Tissue Factor (TF) and TAT levels were tested using ELISA assay in the serum and BALF of ARDS mice in response to EXO-MSCs or EXO-MSC-NTFs treatment.

As described in Example 3 above, MSCs were induced to differentiate into MSC-NTFs (neurotrophic factors secreting MSCs) using a medium-based approach, in which cells were incubated in medium containing (i) 1 mM dibutyryl cyclic AMP (cAMP), (ii) 20 ng/ml human basic fibroblast growth factor (hbFGF), (iii) 5 ng/ml human platelet-derived growth factor (PDGF-AA), and (iv) 50 ng/ml human Heregulin β1.

Animals were weighed daily and were excluded from the study if body weight decreased by 20% from baseline or by more than 10% between measurement. In addition, animals were excluded from the study if any of the following was observed: severe dehydration, lack of movement, skin lesions, continuous tremor or respiratory failure. Animals had free access to food and drinking water throughout the experiment.

To measure the content of specific proteins in MSC small extracellular vesicles (sEVs, EXO-MSCs), 1 ml of sEV enriched fractions were precipitated using ExoQuick-CG (SBI, USA). EV pellets were lysed using M-PER Mammalian Protein Extraction Reagent (ThermoFischer, USA), supplemented with 1:200 Protease Inhibitor Cocktail Set III, EDTA-Free (Calbiochem). Following a 10-minute incubation at room temperature the lysates were frozen and thawed twice to ensure complete lysis. Lysates' protein concentrations were measured using the BCA kit (ThermoFischer, USA) and concentrations of 60-75 ug/ml were used for ELISA assays. AREG and LIF concentration were measured using Quantikine kits (R&D Systems, Minneapolis, MN; Cat #DAR001, DLF00B). HGF and TSG-6 concentration were measured using ELISA kits from RayBiotech, USA (Cat #ELH-HGF-CL-1, ELH-TSG6-1). Signals were quantified using Sunrise plate reader and the Magellan Software V7.2 (Tecan, Switzerland).

The immunomodulatory properties of EXO-MSCs and EXO-MSC-NTFs were evaluated in-vitro by examining inhibition of cytokine secretion by peripheral blood mononuclear cells (PBMCs) in response to activation with phytohemagglutinin (PHA). PBMCs ($5\times10^5$) were stimulated with 10 μg/mL PHA and incubated with EXO-MSCs or EXO-MSC-NTFs ($2\times10^9$ particles) for 4 days in culture. IFNγ and TNFα were measured in the culture supernatant using a commercial ELISA (DuoSet ELISA, R&D Systems, Minneapolis, MN) that was read at 450 nm with Sunrise plate-reader and analyzed by the Magellan Software V7.2 (Tecan, Switzerland).

Figure 13A:
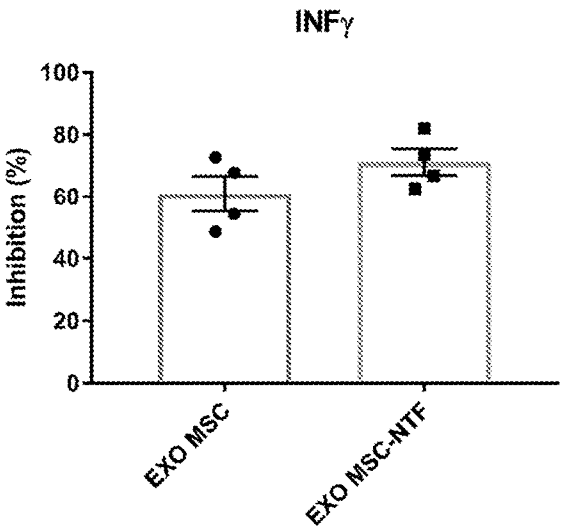
FIG. 13. Immunomodulatory activity of the sEVs as determined by inhibition of IFNγ (FIG. 13A) and TNFα (FIG. 13B) secretion by activated PBMCs. Cell culture supernatant ELISA was performed following incubation with EXO-MSC or EXO MSC-NTF from four independent donors relative to untreated activated PBMCs. Mean±SEM, $*p<0.05$ paired t-test.
Figure 13B:
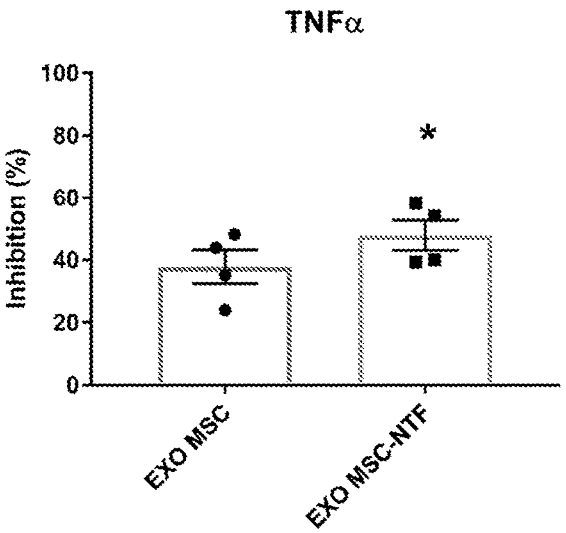

The addition of sEVs, EXO-MSCs or EXO-MSC-NTFs to activated PBMCs resulted in inhibition of IFNγ (FIG. 13A) and TNFα (FIG. 13B) secretion. While there was no significant difference in the ability of EXO-MSCs and EXO-MSC-NTFs to inhibit IFNγ secretion, EXO-MSC-NTFs were significantly more efficient in inhibiting TNFα secretion.

Figure 14A:
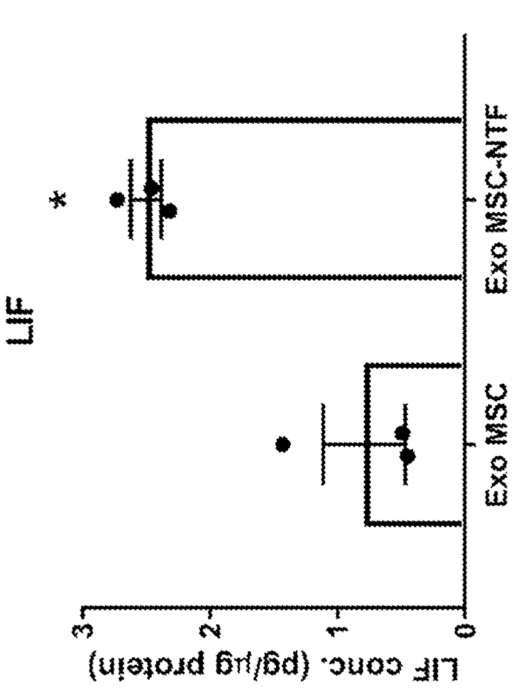
FIG. 14. Differences in protein cargo between EXO-MSC-NTFs and EXO-MSCs. ELISA of EXO-MSCs and EXO-MSC-NTFs lysates from three independent donors displayed higher abundance of (FIG. 14A) LIF and (FIG. 14B) AREG in EXO-MSC-NTFs.
(FIG. 14C) HGF and (FIG. 14D) TSG-6 were detected in both EXO-MSCs and EXO-MSC-NTFs but without significant differences. Mean±SEM, n=3, $*p<0.05$ paired t-test.
Figure 14B:
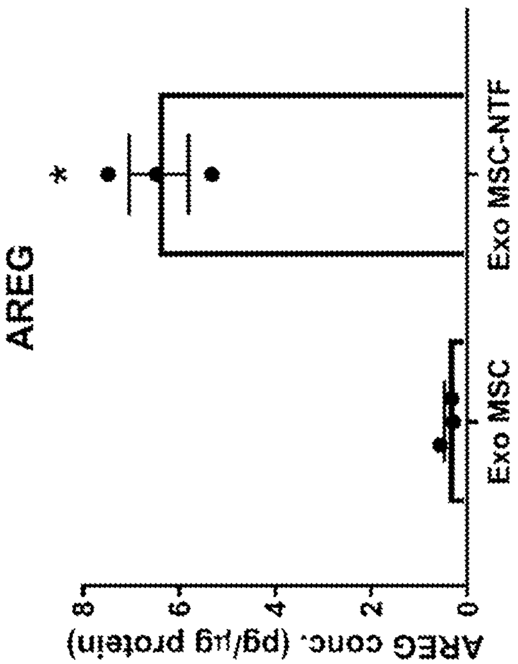
Figure 14C:
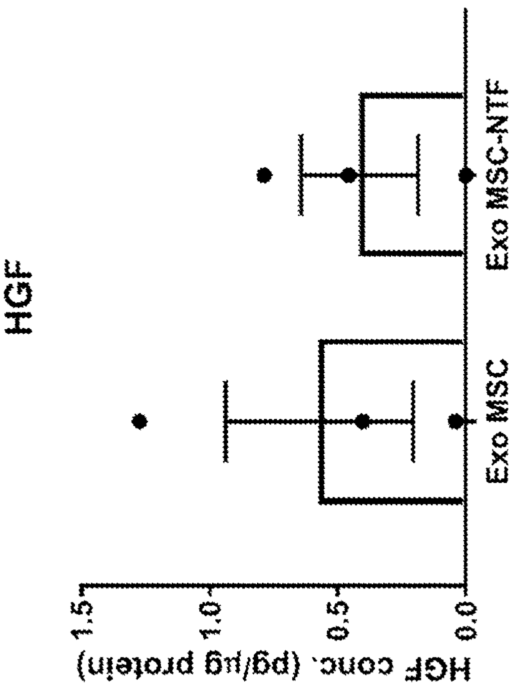
Figure 14D:
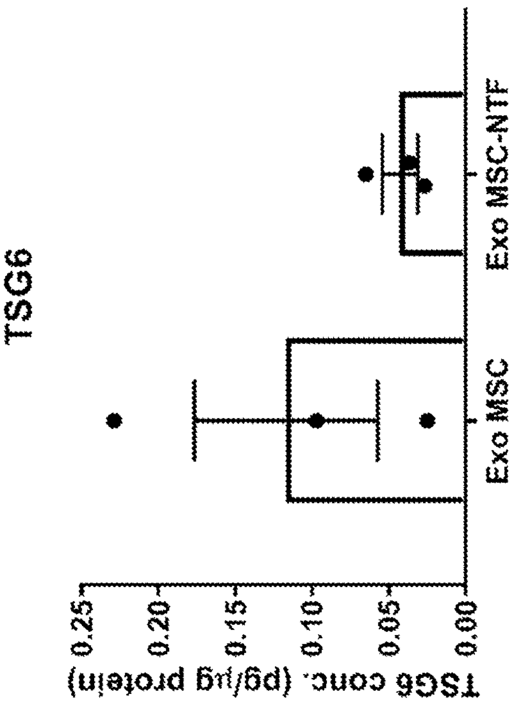

To explore differences between EXO-MSCs and EXO-MSC-NTFs which might contribute to the superior effect of EXO-MSC-NTFs treatment, differences in protein cargo of EXO-MSCs and EXO-MSC-NTFs from three independent donors were evaluated. ELISA measurements revealed that AREG was 16-fold more abundant and LIF was >3 fold more abundant in EXO-MSC-NTF in comparison to EXO-MSC (FIG. 14A, FIG. 14B; p=0.013 and p=0.015, respectively). In addition, HGF and TSG-6 were found to be present in both types of EVs, but without significant differences (FIG. 14C, FIG. 14D).

Table 3 summarized the main protein cargo differences between EXO-MSCs and EXO-MSC-NTFs.

TABLE 3

| Majority protein IDs | Protein names | Gene names | | Student's T-test p-value A_B |
|---|---|---|---|---|
| A1L4H1 | Soluble scavenger receptor cysteine-rich domain-containing protein SSC5D | SSC5D | Down regulated in MSC-NTF vs MSC (<0.05) | 0.001522867 |
| P49747 | Cartilage oligomeric matrix protein | COMP | | 0.007402508 |
| P02452 | Collagen alpha-1(I) chain | COL1A1 | | 0.010384588 |
| Q7Z304 | MAM domain-containing protein 2 | MAMDC2 | | 0.014547382 |
| Q5VTE0; P68104; Q05639 | Putative elongation factor 1-alpha-like 3 | EEF1A1P5 | | 0.015336287 |

TABLE 3-continued

| Majority protein IDs | Protein names | Gene names | | Student's T-test p-value A_B |
|---|---|---|---|---|
| P60903 | Protein S100-A10 | S100A10 | | 0.016648435 |
| P08123 | Collagen alpha-2(I) chain | COL1A2 | | 0.017342827 |
| P09619 | Platelet-derived growth factor receptor beta | PDGFRB | | 0.020643378 |
| Q15113 | Procollagen C-endo-peptidase enhancer 1 | PCOLCE | | 0.02303366 |
| P15144 | Aminopeptidase N | ANPEP | | 0.025159336 |
| O43854 | EGF-like repeat and discoidin I-like domain-containing protein 3 | EDIL3 | | 0.026797162 |
| Q71U36; PODPH8; PODPH7; Q6PEY2 | Tubulin alpha-1A chain | TUBA1A | | 0.028783314 |
| Q92598 | Heat shock protein 105 kDa | HSPH1 | | 0.040291018 |
| P05023 | Sodium/potassium-transporting ATPase subunit alpha-1 | ATP1A1 | | 0.043347997 |
| P62873 | Guanine nucleotide-binding protein G(I)/G(S)/G(T) subunit beta-1 | GNB1 | | 0.044350839 |
| P02748 | Complement component C9 | C9 | Up regulated in MSC-NTF vs MSC (<0.05) | 0.00031156 |
| P08476 | Inhibin beta A chain | INHBA | | 0.001945701 |
| P08254 | Stromelysin-1 | MMP3 | | 0.003022581 |
| P05067 | Amyloid-beta precursor protein | APP | | 0.015430872 |
| P15514 | Amphiregulin | AREG | | 0.024428738 |
| P07602 | Prosaposin | PSAP | | 0.026794496 |
| P20809 | Interleukin-11 | IL11 | | 0.029524275 |
| CON__P13645; P13645 | Keratin, type I cyto-skeletal 10 | KRT10 | | 0.029603145 |
| P01857 | Immunoglobulin heavy constant gamma 1 | IGHG1 | | 0.045674716 |

Example 6. Treatment with Mesenchymal Stem Cells (MSCs) and Mesenchymal Stem Cell Exosomes (EXO-MSCs) for Severe Novel Corona Virus (Covid-19) Pneumonia (NCP)

Primary objectives: To evaluate safety, tolerability and efficacy of intravenous MSCs and/or EXO-MSCs in severe NCP. MSCs and/or EXO-MSCs can also be MSC-NTFs and/or EXO-MSC-NTFs.

Secondary Objectives: To evaluate the efficacy of MSCs and EXO-MSCs using improvement in Critical Treatment Index (CTI); To evaluate the modulation of BAL and blood biomarkers post treatment; To evaluate efficacy of IV MSC administration in severe NCP due to COVID-19 as measured by (a) Ventilator-free days during study period, or (b) Overall Survival/Mortality rate; To evaluate the modulation of cellular and soluble biomarkers after treatment of MSC.

This is a randomized, parallel-design open label study that is conducted in up to 60 participants with severe novel coronavirus pneumonia (NCP) due to COVID-19 at the Screening Visit, at multiple study sites. After providing informed consent and signing a written informed consent document all participants are randomized to the study and observed for a total of 28 days (1 month).

Those subjects that are eligible, based on inclusion and exclusion criteria, are randomized to one of three cohorts: IV MSCs (80-100M MSC/4 ml), IV EXO-MSCs (at least $1.0*10^{10}$ EXO-MSCs/10 ml) or combined IV MSCs and EXO-MSCs to begin daily administration on Days 1, 2, 3, 4 and 5 or on days 1, 3 and 5.

Following the three or five daily treatments, participants are followed up to 28 days. Study safety and physiological parameters as well as biomarkers are obtained.

Figure 15:
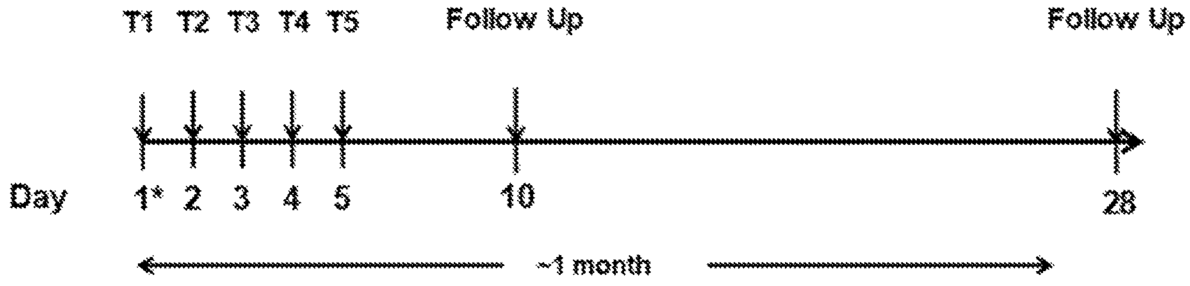
FIG. 15. A schematic illustration of the timeline of an embodiment of a method provided by the present invention: screening visit/baseline assessment and 5 consecutive doses (Days 1, 2, 3, 4, 5) or 3 alternate doses (days 1, 3 and 5) with follow-up assessments through Day 28.

The study comprises a 5-day treatment period followed by a follow-up period up to Day 28 (~1 month, FIG. 15). Treatments are administered within the hospital acute care units or within the ICU. Following each treatment, participants are assessed daily. After receiving the three or five days of treatment all participants are followed for up to 28 days for evaluation of key efficacy and safety assessments. Each participant will thus be followed for a total of about 28 days (1 month) from the first visit.

Eligible subjects who meet inclusion/exclusion criteria are randomized to receive treatment in one of six cohorts in Table 4:

TABLE 4

| Cohort | No of Subjects | Total Dose (vg) |
|---|---|---|
| 1 | 20 | MSCs (80-100M MSC/4 ml) |
| 2 | 20 | EXO-MSCs (at least 1.0 * $10^9$ exosomes/10 ml) |
| 3 | 20 | Combined MSCs and EXO-MSCs |
| 4 | 20 | MSC-NTFs (80-100M MSC/4 ml) |
| 5 | 20 | EXO-MSC-NTFs (at least 1.0 * $10^9$ exosomes/10 ml) |
| 6 | 20 | Combined MSC-NTFs and EXO-MSC-NTFs |

Intravenous MSCs treatment procedure: Procedure for intravenous MSCs (80-100M MSC/4 ml). The product consisted of a 4 ml cell suspension in a 5 ml syringe. It was added to a 100 ml bag of PlasmaLyte-A for infusion over 1 hour.

Intravenous EXO-MSCs treatment procedure: Procedure for intravenous EXO-MSCs (at least 1.0*$10^9$ exosomes/10 ml). The exosome product will consist of 10 ml in a 10 ml syringe. It is added to a 100 ml bag of PlasmaLyte-A for infusion over 1 hour.

Combined Intravenous MSCs and EXO-MSCs treatment procedure: Procedure for combined intravenous MSCs (80-100M MSC/4 ml) and EXO-MSCs (at least 1.0*$10^9$ exosomes/10 ml). The MSC and exosome products are added to separate 100 ml bags of Plasmalyte-A for infusion over 1 hour, at least 2 hours apart.

It should be understood that cells (MSCs, MSC-NTFs) can be administered by intravenous administration, while exosomes (EXO-MSCs, EXO-MSC-NTFs) can be alternatively administered by intravenous, intratracheal, and/or nasal administration (inhalation).

Participants are screened and eligible participants are enrolled. Each subject's participation is followed for approximately 28 days for efficacy and safety assessment that last for approximately 28 days or at completion of study.

Repeat doses (daily consecutive for 5 days or three alternate days) of combined intravenous MSCs (80-100M MSCs/100 ml), iv EXO-MSCs (at least 1.0*$10^9$ exosomes/10 ml) or combined iv MSCs (80-100M MSC/100 ml) and EXO-MSCs (at least 1.0*$10^9$ exosomes/10 ml).

The dose has been shown to be safe for intrathecal transplantation of 100-125×$10^6$ MSC-NTFsin over 200 treated ALS and MS patients. EXO-MSCs are derived from the same MSC cell source.

This study is conducted in patients hospitalized with severe novel coronavirus pneumonia (NCP) due to COVID-19. To be enrolled in this study, participants must meet all inclusion criteria and must not present with any of the exclusion criteria.

Study participants meeting all of the following criteria are allowed to enroll in the study: 1. Males and females ages 18 to 75 years old, inclusive, at the Screening Visit; 2. Laboratory confirmation of 2019-nCoV infection by reverse-transcription polymerase chain reaction (RT-PCR) from any diagnostic sampling source; 3. Pneumonia that is consistent with COVID-19 by baseline chest computed tomography; 4. In accordance with any one of the following: 1) dyspnea (RR ≥30 times/min), 2) finger oxygen saturation ≤93% in resting state, 3) arterial oxygen partial pressure (PaO2)/oxygen absorption concentration (FiO2) ≤300 MMHG, 4) pulmonary imaging shows that the focus progress >50% in 24-48 hours; 5. ARDS associated with COVID-19 infection; 6. Medical necessity for endotracheal intubation and mechanical ventilation; 7. Physician determination that patient is on maximal intensive medical therapy.

Alternatively, Major Inclusion Criteria are 1. Male or female, aged 18-75 years old, inclusive; 2. Laboratory confirmation of 2019-nCoV infection by reverse-transcription polymerase chain reaction (RT-PCR) from any diagnostic sampling source; 3. Acute onset of ARDS, as defined by Berlin criteria and includes: (1) pneumonia or worsening respiratory symptoms within 1 week of known clinical insult (2) bilateral pulmonary opacities on chest X-ray or CT scan not explained by effusions, lobar/lung collapse, or nodules, (3) pulmonary edema not fully explained by cardiac failure or fluid overload, and (4) hypoxemia as defined by PaO2/FiO2 ratio of <300 mmHg; 4. Radiological lung changes (consolidation, ground glass opacities, or bilateral pulmonary infiltration) consistent with COVID-19 ARDS by baseline high-resolution chest computed tomography (HRCT) obtained within 5 days of treatment initiation; 5. Respiratory compromise defined by blood oxygen saturation level (SpO2) <93%.

Study participants meeting any of the following criteria during screening evaluations are excluded from entry into the study: 1. Prior stem cell therapy of any kind; 2. Any history of malignancy within the previous 5 years, except for non-melanoma localized skin cancers (with no evidence of metastasis, significant invasion, or re-occurrence within three years of Screening Visit (Visit 1); 3. Current use of immunosuppressant medication or use of such medication within 6 months of study enrollment. This does not include therapeutic use of corticosteroids or other therapy deemed necessary for the management of COVID-19; 4. Pregnant women or women currently breastfeeding; 5. Cannot obtain informed consent from patient or authorized family member.

Alternatively, Major Exclusion Criteria are: 1. Cannot obtain informed consent from participant or authorized family member; 2. Current use of chronic immunosuppressant medication or use of such medication within 6 months of study enrollment. This does not include acute therapeutic use of corticosteroids or other therapy deemed necessary for COVID-19; 3. Pregnant women or women currently breastfeeding; 4. Prior stem cell therapy; 5. Organ transplant recipients.

Study Assessments.

BRONCHOALVEOLAR LAVAGE AND BLOOD COLLECTION FOR ASSESSMENTS OF BIOMARKERS. Bronchoalveolar lavage and blood serum samples are collected for the detection of biomarkers.

COVID VIRAL LOAD TESTING. Nasopharyngeal swab (NP) to confirm COVID viral genome (as per hospital protocol).

CHEST HIGH RESOLUTION CT SCAN. Chest High Resolution Computerized Tomography (HRCT) as per hospital protocol.

CLINICAL LABORATORY SAFETY TESTS. Clinical laboratory safety tests are monitored throughout the trial at Visits 1-9.

Hematology: Complete blood count (CBC) (Red blood cells [RBC] with Indices, White blood cells [WBCs] with differential and platelet count, hemoglobin [Hb], hematocrit [Ht]).

Serum pregnancy test: hCG

Blood Biochemistry: Sodium (Na), Potassium (K), Calcium (Ca), Bicarbonate (HCO3), blood urea nitrogen (BUN), Creatinine (Cr), Glucose (Gluc), Chloride (Cl), Total cholesterol, high-density lipoprotein (HDL), low-density lipoprotein (LDL), total bilirubin, aspartate aminotransferase (glutamic oxaloacetic transaminase) (AST [GOT]), alanine aminotransferase (glutamic pyruvic transaminase) (ALT [GPT]), alkaline phosphatase (ALP), uric acid.

Coagulation: Prothrombin time (PT), Partial thromboplastin time (PTT), international normalized ration (INR).

Urinalysis—Specific Gravity, pH, glucose, protein, ketones, blood.

Vital Signs measurements (including blood pressure, body temperature, pulse and respiration rate after sitting for at least 3 minutes) are monitored at Screening (Visit 1) and at all in clinic visits through last Visit.

Standard 12-Lead electrocardiogram ECG is performed at Visit 1. ECG results must be manually read, preferably by a cardiologist, and the results entered on the electronic case report form (eCRF).

Daily assessments: Safety and adverse events including clinical progress of ARDS, vitals, laboratory evaluation (CBC and differential, platelet count, BUN, Creatinine, LDH, PT, PTT, INR, Ferritin, D-dimer, ALT, AST, pH, lactate, CK).

Respiratory Physiological Parameters (PaO2/FiO2 ratio).

Collection of blood/serum for biomarkers (Pre-treatment on Days 1, 2, 3, 4, 5 and approximately 6 hours post each treatment).

Inflammatory markers: C-reactive protein (CRP) and Procalcitonin (PCT) and White Blood Cell Differential Count.

Cytokines: IL-2, IL-6, IL-7, G-CSF, IP10, MCP-1, MIP-1a, IL-8 and TNF-α, IL-1-a and IL-1-b, IFN-y.

Biomarkers that reflect the paracrine activity of administered MSCs (VEGF, ANG-1, and KGF). Sequential Organ Failure Assessment (SOFA) score. Acute Physiology and Chronic Health Evaluation II (Apache II) score.

Day 10 (in addition to daily assessments): Nasopharyngeal swab (NP) to confirm presence/absence of COVID viral genome. High-resolution chest computerized tomography (HRCT) to assess change of lung imaging abnormalities compared to baseline (pretreatment, Day 1). Collection of serum/blood biomarker.

Day 28 (in addition to daily assessments): Safety and adverse events (proportion of participants with treatment-related adverse events as assessed by CTCAE v4.0). Ventilator-free days during study period. ICU-free days during study period. Overall Survival/Mortality rate (proportion of deaths from all causes). Clinical Critical Treatment Index.

Pre-Treatment Visits

Visit 1: Screening and Randomization Visit (Day 0).

A written informed consent form (ICF) must be obtained from the participant or legal authorized representative (LAR) before any study-specific screening evaluations are performed.

The following evaluations and procedures are performed: Signed Informed consent (to be obtained by the Principal Investigator [PI] or Sub-Investigator [Sub-I]). Collect demographic data. Medical history. Medical history of COVID and date of diagnosis. Nasopharyngeal swab (NP) to confirm COVID viral genome. High-resolution Chest Computerized Tomography (HRCT). Bronchoalveolar lavage (BAL) collection for biomarkers. Standard 12-Lead electrocardiogram (ECG). Review of prior medications. Vital sign measurements (including blood pressure, body temperature; pulse and respiration rate). Respiratory variables (minute ventilation, respiratory rate, oxygenation index, and PEEP level).

Clinical Critical Treatment Index. No limitation of activities, discharged from hospital=Score 1; Limitation of activities=Score 2; Hospitalized, no oxygen therapy=Score 3; Oxygen by mask or nasal prongs=Score 4; Non-invasive ventilation or high-flow oxygen=Score 5; Intubation and mechanical=Score 6; Ventilation+additional organ support-ECMO, CRRT, pressors=Score 7; Death=Score 8.

Blood collection for hematology (CBC (hematology panel)—hemoglobin, hematocrit, white count (and differential), platelet count), coagulation (PT, PTT, INR), biochemistry evaluations (Sodium, potassium, chloride, glucose, BUN, creatinine, bicarbonate, calcium, total bilirubin, AST, ALT, ALP, uric acid, total cholesterol, HDL, LDL).

Blood collection for serum biomarker analysis (baseline).

Blood collection for a serum pregnancy test (Female participants of childbearing potential).

Urinalysis (Specific gravity, pH, glucose, protein, ketones, blood).

Determine study eligibility, review of Inclusion/Exclusion Criteria.

Randomization of eligible subjects.

Treatment Visits

Visit 1, 2, 3, 4, and 5 (Days 1, 2, 3, 4 and 5) or Visits 1, 3 and 5 (Days 1, 3 and 5): Subjects must continue to meet all inclusion criteria and no exclusion criteria on Day 1 of the study to receive study treatment. If a subject's clinical status changes between screening (Day 0) and Visit 1 (Day 1), some or all of the screening assessments may need to be repeated to assess the subject's eligibility. In such a situation, the medical monitor should be contacted to discuss enrollment into the study.

Pre-treatment assessments (Up to 2 hours before treatment) will include: Vital sign measurements (including Systolic blood pressure (mmHg), body temperature; pulse and respiration rate (per minute); SpO2 Scale 1(%), SpO2 Scale 2(%); Use of air or oxygen. Clinical and radiological progress of ARDS. Safety and adverse events including review of concomitant medications. Blood is collected for hematology (CBC (hematology panel)), coagulation (PT, PTT, INR), biochemistry (sodium, potassium, chloride, glucose, BUN, creatinine). Collection of blood/serum for biomarkers (Days 1, 2, 3, 4, 5 or days 1, 3 and 5 approximately 6 hours post treatment). Inflammatory markers: C-reactive protein (CRP) and Procalcitonin (PCT). Serum markers: IL-2, IL-6, IL-7, IL-8, G-SCF, IP10, MCP-1, MIP-1A and TNF-α, IFN-gamma and IL-1-alpha. Bronchoalveolar lavage—total protein, albumin, IL-1-beta, IL-6, IL-8, TNF-α, SRAGE immune cells: lymphocytes, neutrophils. Biomarker that may reflect the paracrine activity of administered MSCs (ANG-1, TSG-6 and KGF). Cytokine-secreting immune cells: CXCR3+CD4+ T cells, CXCR3+CD8+ T cells, and CXCR3+ NK cells.

Post-treatment, participants will undergo the following: Vital signs are monitored at 2 (±15 minutes), 8 (±15 minutes) and 20 hours (±30 minutes) post-transplantation. Blood is collected 20 hours (±30 minutes) post-transplant for biomarker evaluations. Sequential Organ Failure Assessment (SOFA) score. Acute Physiology and Chronic Health Evaluation II (Apache II) score. Glasgow Coma Scale (GCS) score. Review of adverse events (AEs).

Post Treatment Follow-Up

Visit 7 (Day 10) and 8 (Day 22): At the Day 10 and Day 22 follow-up visits, participants will undergo: Review of concomitant medications. Review of adverse events. Vital sign measurements (including blood pressure, body temperature; pulse and respiration rate). Nasopharyngeal swab (NP) to confirm COVID viral genome. High-resolution Chest CT: change from baseline using standardized scoring. Bronchoalveolar lavage (BAL): biomarker analyses compared to baseline. Blood/serum collection for serum biomarker analysis compared to baseline. Standard 12-Lead ECG. Review of concomitant medications. Review of adverse events (AEs).

Blood collection for hematology (CBC (hematology panel)—hemoglobin, hematocrit, white count (and differential), platelet count), coagulation (PT, PTT, INR), biochemistry evaluations (Sodium, potassium, chloride, glucose, BUN, creatinine, bicarbonate, calcium, total bilirubin, AST, ALT, ALP, uric acid, total cholesterol, HDL, LDL).

Urinalysis (Specific gravity, pH, glucose, protein, ketones, blood).

Visit 9: Day 28 (±5 days) Follow-Up. At Visit 9 post treatment follow-up, all participants will undergo: Review of concomitant medications. Review of adverse events. Vital sign measurements (including blood pressure, body temperature; pulse and respiration rate).

Blood collection for hematology (CBC (hematology panel)—hemoglobin, hematocrit, white count (and differential), platelet count), coagulation (PT, PTT, INR), biochemistry evaluations (Sodium, potassium, chloride, glucose, BUN, creatinine, bicarbonate, calcium, total bilirubin, AST, ALT, alkaline phosphatase, uric acid, total cholesterol, HDL, LDL). Blood collection for a serum pregnancy test (female participants). Urinalysis (Specific gravity, pH, glucose, protein, ketones, blood). Safety and adverse events (proportion of participants with treatment-related adverse events as assessed by CTCAE v4.0). Respiratory variables (minute ventilation, respiratory rate, oxygenation index, and PEEP level). Sequential Organ Failure Assessment (SOFA) score. Acute Physiology and Chronic Health Evaluation II (Apache II) score. Glasgow Coma Scale (GCS) score.

Record the following: Number of days on mechanical ventilation and number of participants successfully weaned from mechanical ventilation. Number of days in ICU. Mortality rate, proportion of deaths from all causes. Number of days free from organ failure to day 28 (cardiovascular, coagulation, hepatic, and renal). Increase in SpO2/FiO2 of 50 or greater compared to the nadir SpO2/FiO2. Time to improvement in oxygenation for at least 48 hours by hospital. Clinical Critical Treatment Index (Improvement Time).

No limitation of activities, discharged from hospital=Score 1; Limitation of activities=Score 2; Hospitalized, no oxygen therapy=Score 3; Oxygen by mask or nasal prongs=Score 4; Non-invasive ventilation or high-flow oxygen=Score 5; Intubation and mechanical=Score 6; Ventilation+additional organ support-ECMO, CRRT, pressors=Score 7; Death=Score 8.

SAFETY FOLLOW-UP. All subjects who are treated or partially treated will have safety and efficacy follow-up for approximately 28 days. Adverse events (AEs) and serious adverse events (SAEs) are followed up.

Investigational Product Information. Mesenchymal Stem Cells (MSC) Product Characteristics.

The MSCs were provided in a ready-to-use treatment package with the appropriate primary and secondary labels. The treatment package consisted of one 5 mL syringe for IV administration. Each treatment package consisted of ready-for-injection syringes containing allogeneic MSCs at a dose of $100\times10^6$ cells in 4 ml.

Syringes were capped with a stopper (not a needle). The 5 mL syringe for IV administration was packed in a pouch.

The treatment package was delivered to the Medical Center in a shipping system container designed for maintaining a temperature of 2-8° C. during shipment. The product was administered to the patient within the established shelf life of the product.

Alternatively, the treatment package consists of one Cryotube containing $130\times10^6$ allogeneic MSC cells/tube for IV administration. The Cryotubes will be shipped in the liquid nitrogen vapor phase and the tube will be thawed by the patient's bed.

The MSCs were administered intravenously by injecting the 4 ml cell suspension from the syringe into a bag with 100 ml Plasmalyte-A and infused over 1 hour.

The patient received all three transfusions with no particular issues. Lab results demonstrated a reduction in CRP and d-dimer. The patient maintained requirement for oxygen, however post-treatment, oxygen saturation increased from 92% to 97% with a reduction in flow from 40 to 30 L. Chest infiltrates persisted. PCR tests for the COVID-19 virus was negative on two occasions.

Mesenchymal Stem Cell Exosomes (EXO-MSCs) Product Characteristics

The EXO-MSCs are provided in a ready-to-use treatment package with the appropriate primary and secondary labels. The treatment package consists of one 10 mL syringe for IV administration. Each treatment package consists of ready-for-injection syringe containing at least $1.0*10^9$ EXO-MSCs in 10 ml.

Syringes are capped with a stopper (not a needle). The 10 mL syringe for IV administration is packed in a pouch.

The treatment packages are delivered to the Medical Center in a shipping system container designed for maintaining a temperature of 2-8° C. during shipment. The product shall be administered to the patient within the established shelf life of the product.

Alternatively, the treatment package consists of one Cryotube containing MSC-exosomes in 10 ml. The cryotube will be shipped on dry ice.

The EXO-MSC-exosomes are administered intravenously by injecting the 10 ml cell suspension from the syringe into a bag with 100 ml Plasmalyte-A and infused over 1 hour.

Prior and Concomitant Therapy

PRIOR THERAPY. Participants who received prior cell therapy of any kind are excluded from the study. In order to minimize the amount and impact of missing data, study investigators will make all reasonable efforts to collect key efficacy and safety data on participants who discontinue treatment or discontinue from the study. All medications taken prior to the first transplantation are recorded as Prior medications.

CONCOMITANT AND EXCLUDED THERAPY. Concomitant medications are those given to the subject during or after the first treatment. All concomitant medications are recorded. Current use of immunosuppressive medication or use of such medication within 6 months of study enrollment are exclusionary. This does not include therapeutic use of corticosteroids or other therapy deemed necessary for the management of COVID-19.

SAFETY REPORTING. For this study, Adverse Events (AEs) and Serious Adverse Events (SAEs) are collected from the time of informed consent through the end of study (Visit 9 or an Early Termination visit). Outcome. The following terms are used during this study: Fatal; Not Recovered/not resolved; Recovering/resolving; Recovered/resolved; Recovered/resolved with sequelae; Unknown; Clinically Significant Laboratory Abnormalities.

Any laboratory abnormalities deemed clinically significant by the Investigator shall be reported on the AE eCRF. A clinically significant abnormality is a confirmed abnormality that is changed sufficiently from screening visit so that in the judgment of the Investigator a change in management is warranted. This alteration may include monitoring the laboratory test further, initiating other diagnostic tests or procedures, changing ongoing treatment, or administering new treatment. Whenever possible, the etiology of the abnormal finding (e.g., anemia) is recorded on the eCRF. Repeated additional tests and/or other evaluations required to establish the significance and etiology of an abnormal result shall be obtained when clinically indicated.

Study Discontinuation. Study or Site Termination.

Conditions may arise during the study that could prompt the study to be halted or the study site to be terminated from participation. Conditions that may prompt such considerations include, but are not limited to, the following: The discovery of unexpected, serious, or unacceptable risk to the participants enrolled in the study. A decision on the part of the Data and Safety Monitoring Board (DSMB) to recommend suspending or discontinuing the study. A decision on the part of Sponsor to suspend, discontinue, or shorten the study.

Study conduct at the study site may warrant termination under conditions that include the following: Failure of Investigator(s) to enroll eligible participants into the study: Failure of Investigator(s) to comply with International Conference on Harmonization (ICH)—Good Clinical Practice (GCP) guidelines, or FDA guidelines and regulations; Submission of false information from the research facility to the Sponsor, the Clinical Monitor, the FDA, or IRB; Insufficient adherence to protocol requirements; A conflict of interest of the Investigator, his/her institution, or site personnel that would negatively impact the integrity of the clinical trial; Institution or IRB under investigation for cause by a regulatory agency.

SUBJECT WITHDRAWAL FROM STUDY. Participants may voluntarily withdraw from the study at any time during the course of the study for any reason, specified or unspecified, and without prejudice. The Investigator will document the reason/circumstances for withdrawal in the appropriate eCRF in a timely manner (preferably within 24-48 hours).

Participants can discontinue from the study for any of the following reasons: For any reason related to safety or tolerability; At the subject's request; At the discretion of the Investigator, if deemed appropriate for any reason; At the discretion of the Sponsor, if deemed appropriate for any reason.

Participants who discontinue from the study for any reason will have follow-up with all relevant evaluations for safety and efficacy including clinical assessments and collection of laboratory study results as set out in this protocol.

The site must document this providing the reason in the End of Study page eCRF in the electronic database. The documentation should include the date the participant withdrew consent/discontinued, the reason for discontinuation. The date documented is considered the last date of contact and thus the participant's last day on the study. Despite discontinuing from the study, if the site becomes aware of any adverse events or SAEs that occur within 12 weeks of the last treatment, they should be recorded in the database Adverse Event log.

TEMPORARY DISCONTINUATION FROM THE STUDY. Study treatment can be temporarily withheld in case of any serious adverse event (SAE) or significant inter-current illness or cell-manufacturing and patient visit scheduling issues.

Assessment of Endpoints.

PRIMARY ENDPOINT. Safety. The primary endpoint is to evaluate the safety and tolerability of 5 consecutive daily or three alternate intravenous doses of allogenic MSCs and/or EXO-MSCs). Safety and adverse events (proportion of participants with treatment-related adverse events as assessed by CTCAE v4.0).

SECONDARY ENDPOINTS. Modulation of BAL and Blood Biomarkers: The efficacy of MSCs and EXO-MSCs cells are evaluated by the modulation of BAL and blood biomarkers following treatment. BAL and blood samples are collected as per the schedule of assessments to evaluate biomarkers before each treatment throughout the study, to evaluate their relationship to treatment with MSCs and EXO-MSCs. Improvement time of Clinical Critical Treatment Index. Time to improvement in oxygenation for at least 48 hours by hospital. Number of Days in the ICU. Mortality rate, proportion of deaths from all causes. Number of days on mechanical ventilation and number of participants successfully weaned from mechanical ventilation.

Statistical Methods and Sample Size Determination.

Sample Size Determination. No formal sample size calculation is performed. Efficacy and safety data on 60 subjects will provide information to inform the design of a future randomized clinical study.

Statistical Methods. Summaries for continuous variables will include the sample size, mean, standard deviation, median, minimum, and maximum. Minima and maxima are reported with the same precision as the raw values; means, standard deviations, and medians are presented to one additional decimal place than reported in the raw values. Summaries for discrete variables will include frequencies and percentages. All percentages are rounded to one decimal place (i.e., XX.X %). The baseline visit is defined as the last non-missing measure prior to initiation of investigational treatment (first treatment at Visit 1, Day 0).

A detailed Statistical Analysis Plan (SAP) is completed prior to the first subject being treated.

Analysis Population.

The primary, secondary and exploratory efficacy endpoints are analyzed using the modified intent to treat (mITT) and Efficacy Evaluable (EE) populations. The mITT population is defined in this study as all participants who received at least one treatment and have at least one assessment post baseline. Baseline is defined as the most recent assessment prior to receiving the first transplantation on Day 1, at Visit 2. The EE population is defined as a subset of the mITT population that receive all 5 treatments and do not have any important protocol deviations impacting efficacy evaluation.

If the EE population is identical or very similar to the mITT population, analyses may only be generated for the mITT population.

All safety analyses are conducted on the Safety Population, which is defined as all participants who were enrolled and had at least one transplantation performed.

Efficacy Analyses. Efficacy analyses are performed using the modified mITT and EE populations as described above.

Safety analyses. All safety analyses are based upon the Safety Population.

All AEs are coded to System Organ Class (SOC) and Preferred Term (PT) using the Medical Dictionary for Regulatory Activities (MedDRA®). The number of treatment-emergent adverse events (TEAEs) and the number of participants with any TEAEs (along with percentages) are tabulated by SOC and PT.

A TEAE is an AE that occurs for the first time after initiation of treatment or if it had occurred prior to treatment, worsens in severity after initiation of treatment.

Separate summaries are provided for the following categories of AEs: TEAEs, TEAEs by severity, Treatment-related TEAEs, Serious TEAEs.

When evaluating changes in safety parameters, Baseline is defined as the last measurement prior to initiation of the first treatment.

Abnormalities in hematology, blood chemistry and ECG assessments are summarized.

HRCT is assessed for study safety at baseline and at the end of the study.

Biomarker Analysis. Bronchoalveolar lavage (BAL) and/or blood samples are analyzed for the concentration of biomarkers and their relationship to clinical outcomes at each visit. In addition, relationships between biomarkers and clinical outcomes are evaluated to determine if any biomarkers can be predictive of treatment outcome. Analyses are detailed in the SAP.

Example 7: Study Protocol for MSC-NTF Exosomes Treatment in a Mouse Model of Lung Injury

Background

Lung indications that may be targeted by EXO-MSC-NTFs include Adult Respiratory Distress Syndrome (ARDS); Interstitial Pulmonary Fibrosis (IPF); Bronchopulmonary Dysplasia (BPD); and Chronic Obstructive Pulmonary Disease (COPD).

ARDS affects 150,000 individuals in the USD per year (16/100,000 population) and carries a 30-70% mortality during the acute episode. Potential benefits of EXO-MSC-NTFs therapy could include reduced mortality, decreased ICU or hospital stay, improved ventilatory status and reduced need for ventilatory support. ARDS is related to shock, sepsis, pneumonia (including COVID-19), transfusions, gastric aspiration, and trauma.

IPF affects 50,000 individuals in the US per year (10,100,000) and has a median survival of 2-3 years after diagnosis. Potential benefits of EXO-MSC-NTFs therapy could include reduced mortality, decreased ICU or hospital stay, improved ventilatory status, reduced need for lung transplantation and reduced need for ventilatory support.

BPD is seen in 35% of births less than 28 weeks' gestation and affects approximately 18,000 infants per year in the US. The mortality rate of BPD is approximately 40-60% in infants less than 1500 grams birth weight. Potential benefits of EXO-MSC-NTFs therapy could include reduced mortality, decreased ICU or hospital stay, improved ventilatory status, improved lung development, and reduced need for ventilatory support.

COPD affects 15 million individuals in the US (44.3/100,000 population). It carries a 5-year mortality of 40-70% and a 2-year mortality of 50% in severe COPD. Potential benefits of EXO-MSC-NTFs therapy could include reduced mortality, decreased ICU or hospital stay, improved ventilatory status, and reduced need for ventilatory support.

Other Animal Models

Bronchopulmonary dysplasia (BPD) is the most common chronic lung disease of very preterm infants. BPD interrupts lung development and has serious long-term respiratory complications that reach beyond childhood and into adult life. Understanding of BPD and the potential of developing therapeutic strategies have arisen from large (baboons, sheep, and pigs) and small (rabbits, rats, and mice) animal models. These models primarily aim at inducing alveolar simplification similar to what is seen in infants with BPD.

Various mouse models of BPD, focus mainly on the hyperoxia-induced lung injury. There are also hypoxia, hypoxia/hyperoxia, inflammation-induced, and transgenic models.

Animal models of COPD are mainly induced in mice, guinea pigs and rats. In most of the studies, this model is induced by exposure to cigarette smoke (CS), intra-tracheal lipopolysaccharide (LPS) and intranasal elastase. There are variations in time course and dose of inducers used in different studies. The main measured parameters are lung pathological data and lung inflammation (both inflammatory cells and inflammatory mediators) in most of the studies and tracheal responsiveness (TR) in only few published studies (Ghorani V, Boskabady M H, Khazdair M R, Kianmeher M. Experimental animal models for COPD: a methodological review. Tob Induc Dis. 2017 May 2; 15:25, incorporated herein by reference).

EXO-MSC-NTFs produce their unique effects in part through paracrine secretion of Vascular endothelial growth factor (VEGF), Amphiregulin (AREG) and Leukemia inhibitory factor (LIF).

VEGF may play a role in acute and resolving lung injury through beneficial effects on alveolar type II epithelial cells. AREG modulates murine lung recovery and fibroblast function following exposure to agriculture organic dust, protects against LPS-induced acute lung injury in mice, possibly by maintaining lung tissue homeostasis, inhibition of TNF-alpha induced alveolar epithelial cells death through EGFR signaling, increasing the number of pathogenic memory T helper-2 cells control the airway fibrotic responses. LIF plays an important role in reducing chronic airway inflammation, protecting the lung during viral pneumonia, and is reduced by chronic cigarette smoking.

Study Aim

The aim of this study was to explore the efficacy of bone marrow derived mesenchymal stem (MSCs) and EXO-MSC-NTFs (via intratracheal or aerosol inhalation) in another mouse model of inflammation and fibrosis, the mouse model of Bleomycin.

Bleomycin, a chemotherapeutic antibiotic produced by the bacterium "*Streptomyces verticillus*", is used as an agent to induce experimental lung fibrosis. It causes inflammatory and fibrotic reactions within a short period of time, mainly after intratracheal instillation. The initial elevation of pro-inflammatory cytokines is followed by increased expression of pro-fibrotic markers and collagen accumulation, with a peak around day 14.

Stem cell derived EVs have been tested in experimental lung injury models, including models of asthma, ARDS, COPD, IPF, pneumonia, pulmonary artery hypertension, and silicosis, with promising results (Cruz F F, Rocco P R M. Stem-cell extracellular vesicles and lung repair. Stem Cell Investig. 2017 21; 4:78, incorporated herein by reference). Common pathologies for these lung diseases include inflammation and fibrosis.

An improvement on all clinical parameters tested is expected with MSCs and an enhanced effect with EXO-MSC-NTFs as compared to control (PBS).

Study Design.

1. Model: Murine Model of Bleomycin-Induced Lung Injury

Pulmonary injury was induced with a single intratracheal injection of 3 U/kg bleomycin sulfate solution in C57bl mice.

2. Treatment

Treatment was provided intratracheal either in the inflammatory phase (day 1 and day 5) or in the fibrotic phase (day 7 and day 10) to evaluate separately the effect of the exosomes on inflammation and fibrosis.

In addition, one group of mice received treatment via inhalation for initial evaluation of this Route of Administration (RoA).

3. Study Groups—

TABLE 5

| Group number | Experimental group | N | Treatment | Treatment frequency | Study duration | ROA |
|---|---|---|---|---|---|---|
| 1 | Bleomycin | 10 | EXO-MSC-NTFs (3 × 10^10; 50 µl) | Day 1 and 5 | 14 days | Intratracheal |
| 2 | Bleomycin | 10 | EXO-MSCs (3 × 10^10; 50 µl) | Day 1 and 5 | 14 days | Intratracheal |
| 3 | Bleomycin | 10 | EXO-MSC-NTFs (3 × 10^10; 50 µl) | Day 7 and 10 | 14 days | Intratracheal |
| 4 | Bleomycin | 10 | EXO-MSCs (3 × 10^10; 50 µl) | Day 7 and 10 | 14 days | Intratracheal |
| 5 | Bleomycin | 10 | PBS (50 µl) | Day 1 and 5 | 14 days | Intratracheal |
| 6 | Bleomycin | 10 | PBS (50 µl) | Day 7 and 10 | 14 days | Intratracheal |
| 7 | Bleomycin | 10 | EXO-MSC-NTFs 5 ml/20 min | Daily (days 5-12) | 14 days | Inhalation (initial evaluation of this ROA) |
| 8 | Control (PBS instillation) | 5 | | | 14 days | Intratracheal |

Analyses

- Oxygen saturation throughout the study (4-5 time points).
- Collection of BAL fluid and serum at the end of experiment (Measurement of inflammatory factors in BAL fluid and serum).
- Lung Histopathology and quantification of fibrosis by Ashcroft score—a score of pulmonary fibrosis ranging from 0 (normal lung) to 8 (total fibrous obliteration of the field (Ashcroft T, Simpson J M, Timbrell V (1988) Simple method of estimating severity of pulmonary fibrosis on a numerical scale. Journal of clinical pathology. 1988; 41(4):467-70, incorporated herein by reference).
- Expression of a panel of fibrosis and cytokines mRNA in lung tissue (NanoString analysis).
- Collagen content in the lung tissue.

Results

The results confirm a positive effect on oxygen saturation and weight of mice treated with EXO-MSCs and EXO MSC-NTFs by the intratracheal route of administration as compared to the control groups.

Figure 16A:
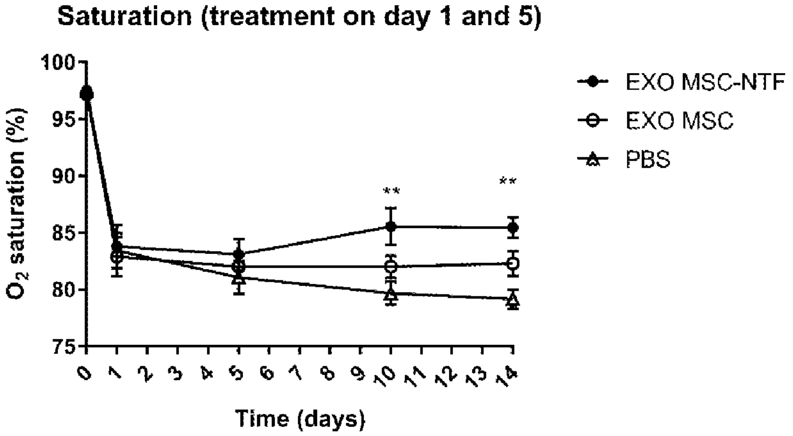
FIG. 16A, FIG. 16B and FIG. 16C represent oxygen saturation
Figure 16B:
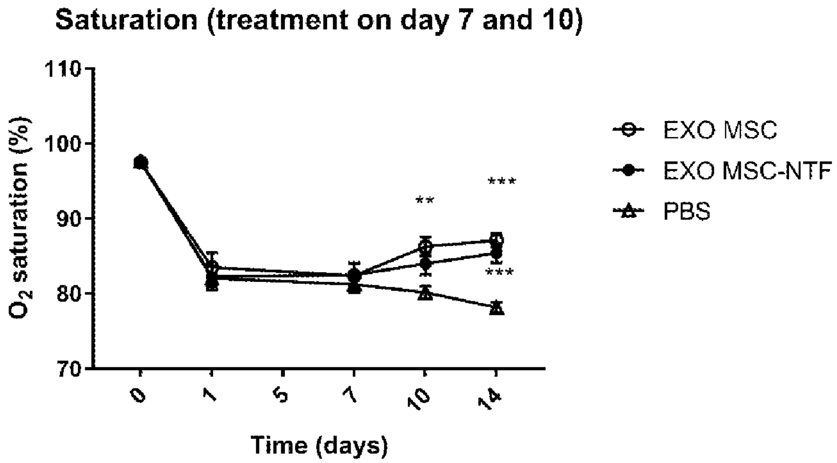
Figure 16C:
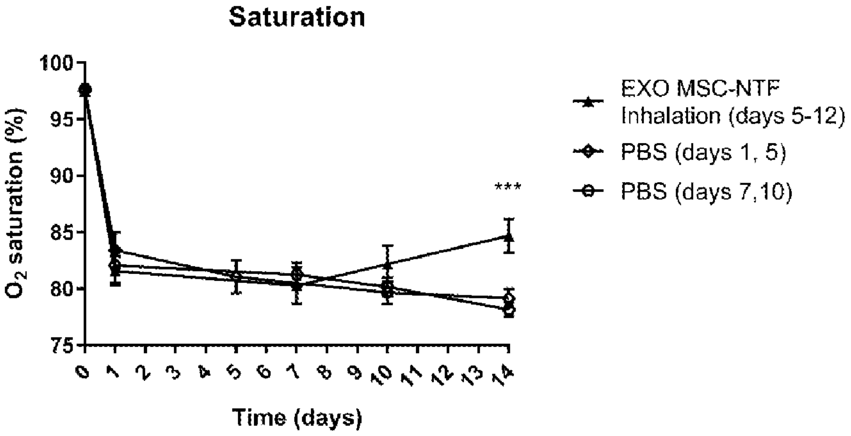

Significant improvement on oxygen saturation of mice treated with EXO-MSC-NTFs as compared to controls was provided by both treatment schedules (days 1 and 5 and days 7 and 10, FIG. 16A and FIG. 16B) while in the day 1 and 5 schedule, EXO-MSC-NTFs displayed a superior effect over EXO-MSCs. EXO-MSC-NTFs treatment by inhalation provided a significant oxygenation benefit as compared to controls (FIG. 16C and FIG. 16F).

Figure 16D:
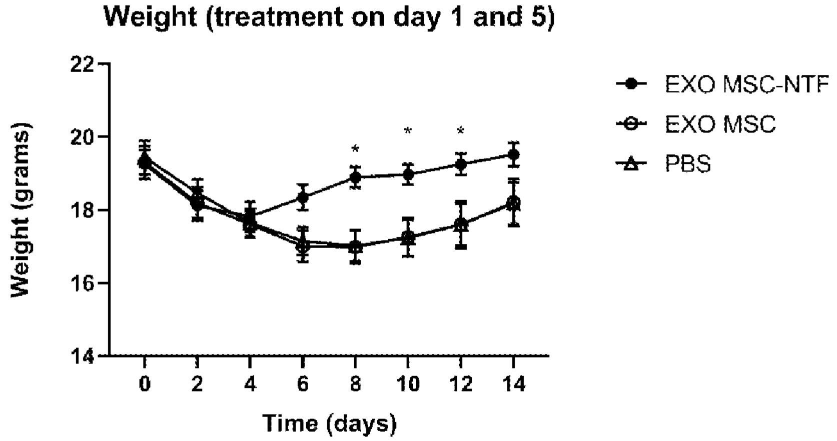
FIG. 16D, FIG. 16E and FIG. 16F represent weight $*p<0.05$, $p<0.01$, $*p<0.001$.
Figure 16E:
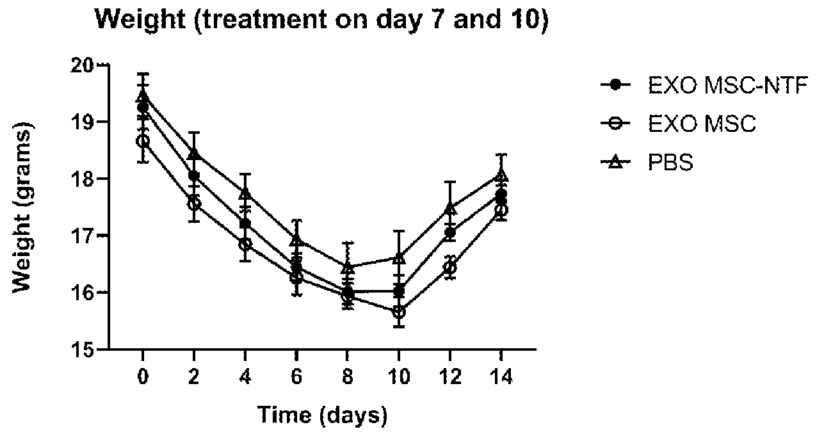
Figure 16F:
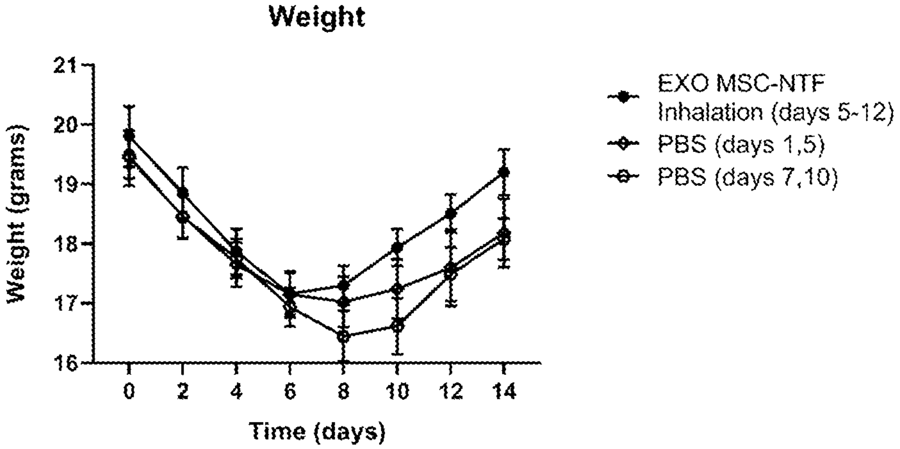

Significant improvement on weight gain was provided only by EXO-MSC-NTFs on the days 1 and 5 treatment schedule FIG. 16D).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a lung condition or a symptom thereof in a patient in need, comprising administering to the patient a therapeutically effective regime of a pharmaceutical composition comprising an active agent selected from the group consisting of (a) a plurality of multipotent mesenchymal stem cells secreting neurotrophic factors (MSC-NTFs) (b) a plurality of small extracellular vesicles (sEVs) derived from MSC-NTFs defined EXO-MSC-NTFs, and (c) a combination of MSC-NTFs and EXO-MSC-NTFs, wherein said NTFs comprise vascular endothelial growth factor (VEGF), amphiregulin (AREG) and leukemia growth factor (LIF).

2. The method according to claim 1, wherein said lung condition comprises a viral lung infection or a non-viral lung infection.

3. The method of claim 1, wherein said active agent is MSC-NTFs.

4. The method of claim 1, wherein said active agent is EXO-MSC-NTFs.

5. The method of claim 1, wherein said pharmaceutical composition comprising an active agent comprises a combination of MSC-NTFs and EXO-MSC-NTFs.

6. The method of claim 1, wherein said pharmaceutical composition comprises about $10^9$ to about $10^{13}$ EXO-MSC-NTFs.

7. The method of claim 1, wherein said therapeutically effective regime comprises repeated administration of the active agent on different days, wherein the repeated administration comprises administration on consecutive days, or alternate days.

8. The method of claim 7, wherein said repeated administration comprises administration on at least five different days.

9. The method of claim 7, wherein said repeated administration is on day 1, day 3 and day 5.

10. The method of claim 1, wherein said pharmaceutical composition further comprises an excipient.

11. The method according to claim 1, wherein the volume of the pharmaceutical composition is between about 100 mL to about 120 mL.

12. The method according to claim 1, wherein said administration of the pharmaceutical composition comprises systemic administration, intravenous administration, intranasal administration, inhalation administration, intratracheal administration, direct injection administration or any combination thereof.

13. The method of claim 1, wherein said symptom is selected from the group consisting of pneumonia, acute respiratory distress syndrome (ARDS), interstitial pulmonary fibrosis (IPF), bronchopulmonary dysplasia (BPD), chronic obstructive pulmonary disease (COPD), multi-organ failure, fever, dry cough, fatigue, sputum production, loss of smell, shortness of breath, reduced oxygen saturation, muscle pain, joint pain, sore throat, headache, chills, nausea, vomiting, nasal congestion, diarrhea, inflammation and fibrosis.

14. The method of claim 13, wherein said symptom is pneumonia, ARDS or combination thereof.

15. The method of claim 2, wherein said viral lung infection is selected from the group consisting of a Coronavirus infection, a severe acute respiratory syndrome (SARS) infection, a Middle East respiratory syndrome (MERS) infection, an Influenza virus infection, an Ebola virus infection, a rabies infection, a West Nile virus infection, a dengue virus infection, a respiratory syncytial virus (RSV) infection, and a Zika virus infection.

16. The method of claim 4, wherein said EXO-MSC-NTFs, when compared to multipotent mesenchymal stem cells (EXO-MSCs):

(i) comprise less of at least one protein selected from the group consisting of A1L4H1, P49747, P02452, Q7Z304, Q5VTE0, P68104, Q05639, P60903, P08123, P09619, Q15113, P15144, O43854, Q71U36, P0DPH8, P0DPH7, Q6PEY2, Q92598, P05023, and P62873, or (ii) comprise more of at least one protein selected from the group consisting of P02748, P08476, P08254, P05067, P15514, P07602, P20809, CON_P13645, P13645, and P01857.

17. The method of claim 16, wherein said EXO-MSC-NTFs, when compared to EXO-MSCs:

(i) comprise less of A1L4H1, P49747, P02452, Q7Z304, Q5VTE0, P68104, Q05639, P60903, P08123, P09619, Q15113, P15144, O43854, Q71U36, P0DPH8, P0DPH7, Q6PEY2, Q92598, P05023, and P62873 proteins, and (ii) comprise more of P02748, P08476, P08254, P05067, P15514, P07602, P20809, CON_P13645, P13645, and P01857 proteins.

18. The method of claim 4, wherein said EXO-MSC-NTFs comprise:

(i) 2.46 to 2.73 pg of Leukemia inhibitory factor (LIF) protein per μg of total proteins, (ii) 5.33 to 7.48 pg of Amphiregulin (AREG) protein per μg of total proteins, (iii) 0.45 to 0.78 pg of hepatocyte growth factor (HGF) protein per μg of total proteins, or (iv) 0.027 to 0.065 pg of tumor necrosis factor-inducible gene 6 protein (TSG6) protein per μg of total proteins.

19. The method of claim 18, wherein said EXO-MSC-NTFs comprise:

(i) 2.46 to 2.73 pg of Leukemia inhibitory factor (LIF) protein per μg of total proteins, (ii) 5.33 to 7.48 pg of Amphiregulin (AREG) protein per μg of total proteins, (iii) 0.45 to 0.78 pg of hepatocyte growth factor (HGF) protein per μg of total proteins, and (iv) 0.027 to 0.065 pg of tumor necrosis factor-inducible gene 6 protein (TSG6) protein per μg of total proteins.

* * * * *